(12) United States Patent
Shroff et al.

(10) Patent No.: US 8,279,329 B2
(45) Date of Patent: Oct. 2, 2012

(54) STRUCTURED ILLUMINATION FOR IMAGING OF STATIONARY AND NON-STATIONARY, FLUORESCENT AND NON-FLUORESCENT, OBJECTS

(75) Inventors: Sapna Shroff, Rochester, NY (US); David R. Williams, Rochester, NY (US); James Fienup, Rochester, NY (US)

(73) Assignee: University of Rochester, Rochester, NY (US)

( * ) Notice: Subject to any disclaimer, the term of this patent is extended or adjusted under 35 U.S.C. 154(b) by 886 days.

(21) Appl. No.: 12/100,723

(22) Filed: Apr. 10, 2008

(65) Prior Publication Data
US 2009/0046164 A1    Feb. 19, 2009

Related U.S. Application Data

(60) Provisional application No. 60/907,579, filed on Apr. 10, 2007.

(51) Int. Cl.
*H04N 5/222* (2006.01)

(52) U.S. Cl. ...................................................... 348/370

(58) Field of Classification Search .................. 348/370; 600/476; 356/456, 603–607; 235/454; 382/154, 382/284
See application file for complete search history.

(56) References Cited

U.S. PATENT DOCUMENTS

| | | |
|---|---|---|
| 2003/0071124 A1 * | 4/2003 | Tsikos et al. ................... 235/454 |
| 2005/0201614 A1 * | 9/2005 | Rice et al. ...................... 382/154 |
| 2005/0275847 A1 * | 12/2005 | Moshe ............................ 356/456 |
| 2006/0058682 A1 * | 3/2006 | Miller et al. ................... 600/476 |
| 2007/0064245 A1 * | 3/2007 | Yoshino et al. ................ 356/603 |

* cited by examiner

*Primary Examiner* — Chieh M Fan
*Assistant Examiner* — Akshay Trehan
(74) *Attorney, Agent, or Firm* — Blank Rome LLP

(57) ABSTRACT

An object to be imaged is illuminated with a structured (e.g., sinusoidal) illumination at a plurality of phase shifts to allow lateral superresolution and axial sectioning in images. When an object is to be imaged in vitro or in another situation in which the phase shifts cannot be accurately determined a priori, the images are taken, and the phase shifts are estimated a posteriori from peaks in the Fourier transforms. The technique is extended to the imaging of fluorescent and non-fluorescent objects as well as stationary and non-stationary objects.

46 Claims, 11 Drawing Sheets (a)          (b)

(a)          (b)

(a)        (b)

(a)        (b)

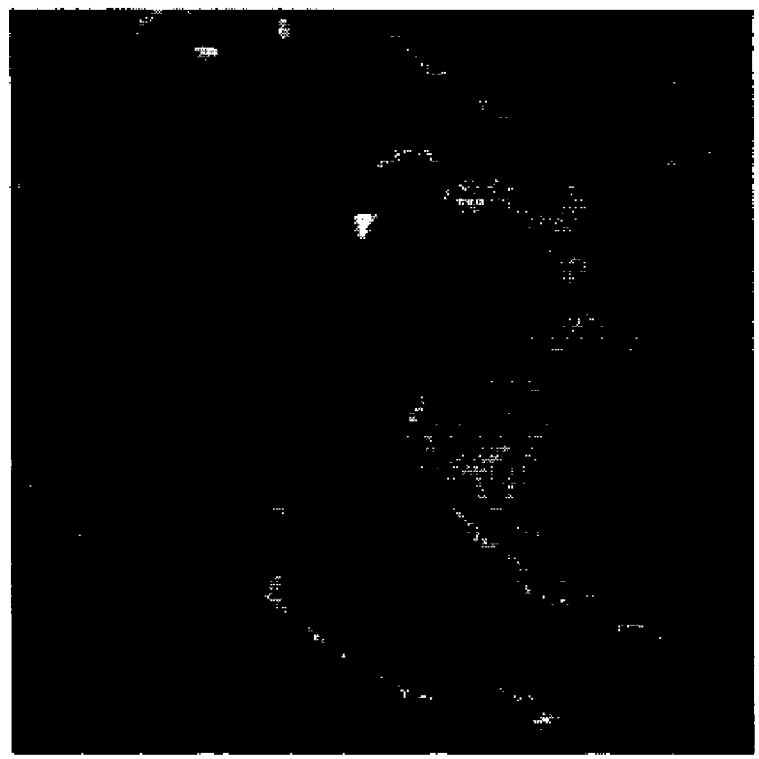
Figure 28.
Fig. 29
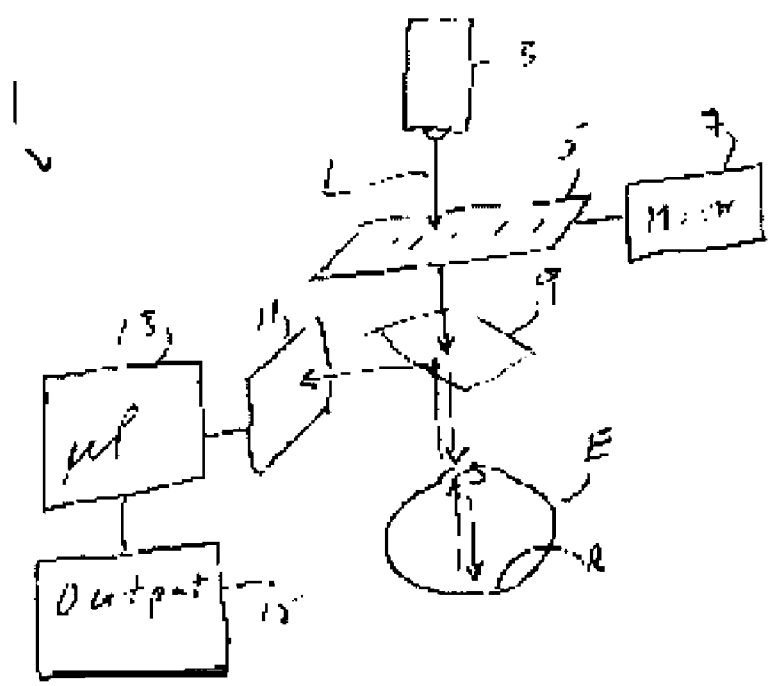

STRUCTURED ILLUMINATION FOR IMAGING OF STATIONARY AND NON-STATIONARY, FLUORESCENT AND NON-FLUORESCENT, OBJECTS

REFERENCE TO RELATED APPLICATION

The present application claims the benefit of U.S. Provisional Patent Application Ser. No. 60/907,579, filed Apr. 10, 2007, whose disclosure is hereby incorporated by reference in its entirety into the present disclosure.

STATEMENT OF GOVERNMENT INTEREST

The work leading to the present invention was supported by NIH Grant No. EY 001319. The government has certain rights in the invention.

FIELD OF THE INVENTION

The present invention is directed to structured illumination imaging and its application to stationary and non-stationary, fluorescent and non-fluorescent objects. A particular case is in vivo imaging, particularly retinal imaging.

DESCRIPTION OF RELATED ART

Structured illumination imaging is a technique used for lateral superresolution and axial optical sectioning (3D imaging). Images of objects such as cells, tissue, fibers, etc are often blurred by the limited size of the numerical aperture of the microscope and the out of focus light. Techniques for superresolution and optical sectioning reveal an abundance of information which is not accessible to scientists with conventional methods of imaging. These imaging techniques can be used in clinical imaging, life science research, biotechnology, semiconductor industry and others areas of imaging.

In this technique the object is illuminated by a sinusoidally patterned illumination instead of the conventional uniform illumination. Several images are taken with the phase of the sinusoid shifted by small amounts. These images are processed to give images of the object with lateral superresolution or axial sectioning (3D imaging).

The lateral superresolution aspect has so far been applied only to stationary fluorescent objects.

The axial sectioning technique is being used in microscopy for in vitro objects. Currently there are at least two companies that manufacture microscopes equipped with structured illumination imaging—ApoTome by the Carl Zeiss Microimaging Inc. and OptiGrid® by Qioptiq Imaging Solutions. These are used for stationary fixed specimens on slides. They cannot image objects in vivo.

In a separate field of endeavor, it is known to image the retina and perform later superresolution and axial sectioning on the retina. However, the retina in vivo is not significantly fluorescent by nature and is never completely stationary. Therefore the advantages of structured illumination imaging have not yet been extended to retinal imaging.

The human retina is a complex structure comprising of millions of cells and many cell types. Many diseases such as age-related macular degeneration, diabetic retinopathy and glaucoma that afflict vision can be diagnosed by detecting their effects on the retina. In the past few years, the vision community has taken significant efforts to image the human retina in vivo. Non-invasive, in vivo imaging makes the study of healthy retinal structure and function possible. It also permits early detection and diagnosis of retinal diseases and hence increases the likelihood and effectiveness of treatment.

For many years doctors have used the ophthalmoscope and fundus camera to non-invasively image the retina in vivo. These are low magnification, wide field of view images. Experts can use these images to identify and diagnose diseases in moderately advanced stages. However it is not possible to use them to detect diseases in their early stage, to detect microscopic retinal damage, or to study the cellular structure of a healthy retina.

The past few years have seen the emergence of high-resolution imaging techniques permitting retinal imaging at a cellular level. Adaptive optics is one such technique that has been applied to a flood illuminated retinal imaging system. Adaptive optics corrects the aberrations of the eye. The optical media in the eye in front of the retina, consisting of the vitreous, the lens, the aqueous, the cornea and the tear film, add optical aberrations to images of the retina. When the pupil aperture is small and undilated, such as 3 mm in diameter, mild aberrations are not significant enough to demand correction. But when the pupil is dilated to 6-8 mm in diameter for retinal imaging, even small aberrations add significant blur to the image. Adaptively sensing these aberrations and correcting them is crucial to getting close to diffraction limited, aberration-free retinal images with micron resolution. Adaptive optics has also been integrated into scanning laser ophthalmoscopes and optical coherence tomography setups. It is now possible to resolve cells that are larger than 2 microns like cones, ganglion cells, retinal pigment epithelium cells, blood vasculature, etc.

But there are several structures that are smaller than 2 microns in size such as rods, foveal cones, fine blood capillaries, ganglion cell axons and dendrites, etc., which have been observed in vitro, but are not easily resolved in vivo for the human retina in most instruments. The wavelength used for imaging and the numerical aperture of the imaging system are the two factors that limit the resolution of the system. The limiting aperture in imaging the retina is the pupil of the eye. It is not possible to dilate a patient's pupil greater than 6-8 mm diameter. Hence the frequencies that are captured by the optical imaging system are limited by the size of this aperture of the eye. In order to image the higher spatial frequency structures in the retina, it is essential to somehow effectively increase the size of this aperture. Therefore, there is a great need to obtain lateral superresolution in retinal imaging.

The axial resolution of an imaging system is also limited similarly by diffraction. Using adaptive optics, it is possible to reduce the effect of aberrations of the eye. But the axial resolution remains unchanged. In most in vivo imaging of the retina, the light scattered from the cornea and lens and the out of focus light from different planes in the retina often results in low contrast of the images. Precise axial optical sectioning is very critical in order to image axially specific regions of the thick retina, such as a particular ganglion cell. The ability to reject the out of focus light is very important to enable the scientist to pick out one layer of cells from a haze of multiple superimposed layers of cells. The retinal pigment epithelial cells emit very weak fluorescence. This signal is weak enough to be lost in most wide field imaging systems. But a system which provides optical sectioning should be able to reject the out of focus light enough to enable the imaging of retinal pigment epithelial cells in vivo. Confocal imaging systems provide optical sectioning capabilities. But they involve elaborate and expensive equipment. Structured-illumination-based axial sectioning setups are several times less expensive.

More generally, it is often necessary to image tissue and cells or materials which do not fluoresce naturally. Traditionally it is necessary to add artificial fluorophores to the object to enable the use of techniques like structured illumination. Often tissues, cells and semiconductor chips may be damaged and change in structural and functional composition due to the addition of fluorophores. This is often inadvisable for scientific research.

Yet another issue is that sinusoidal illumination imaging for superresolution and axial sectioning has only been implemented on stationary specimens such as fixed slides on a vibration-free microscope. (As will be explained below, the use of sinusoidal imaging is illustrative rather than limiting.) The processing requires very accurate knowledge of the phase shifts of the sinusoid in each image in order to recover the three overlapping copies of the object Fourier transform. Usually these phase shifts are imparted in definite known steps using expensive, calibrated, precision actuation equipment. However, it is often necessary to image moving objects, such as the in vivo retina, which show substantial inter-frame rigid body motion. Hence it is not possible to impart known phase shifts of definite step sizes to such a randomly moving object specimen.

SUMMARY OF THE INVENTION

It is therefore an object of the invention to make the imaging of stationary fluorescent objects more robust by improving phase calibration.

It is another object of the invention to apply structured illumination to moving fluorescent objects.

It is still another object of the invention to apply structured illumination to stationary and moving non-fluorescent objects.

It is yet another object of the invention to apply structured illumination to in vivo imaging and in particular to in vivo retinal imaging.

To achieve the above and other objects, the present invention is directed to a technique in which an object to be imaged is illuminated with a structured (e.g., sinusoidal) illumination at a plurality of phase shifts to allow superresolution imaging. When an object is to be imaged in vivo or in another situation in which the phase shifts cannot be accurately determined a priori, the images are taken, and the phase shifts are estimated a posteriori from peaks in the Fourier transforms. The technique is extended to the imaging of non-fluorescent objects such as the retina of the human eye. Unknown phase shifts can occur in a variety of ways, such as movement of the object to be imaged or improperly calibrated equipment; the present invention can estimate any such phase shifts.

The structured illumination is typically, but not necessarily, sinusoidal. Any periodic illumination will do. Examples are $\sin \theta$, $1 + \sin \theta$, $1 + \sin^2 \theta$, and a square wave (binary or Ronchi grating). Some examples will introduce additional frequency terms that should be handled in the calculations, but will not affect phase estimation. Also, the illumination can be periodic in two dimensions, e.g., periodic at two orthogonal angles or at three angles offset by 120°.

The invention can be applied to imaging of the retina or other tissues, to in vivo and in vitro imaging of the tissues, and to non-biological imaging such as inspection of semiconductor chips.

BRIEF DESCRIPTION OF THE DRAWINGS

Preferred embodiments of the present invention will be set forth in detail with reference to the drawings, in which:

FIG. 28 shows a sectioned image produced by Zeiss ApoTome; and

FIG. 29 shows a setup on which the preferred embodiments can be implemented.

DETAILED DESCRIPTION OF THE PREFERRED EMBODIMENTS

Figure 1:
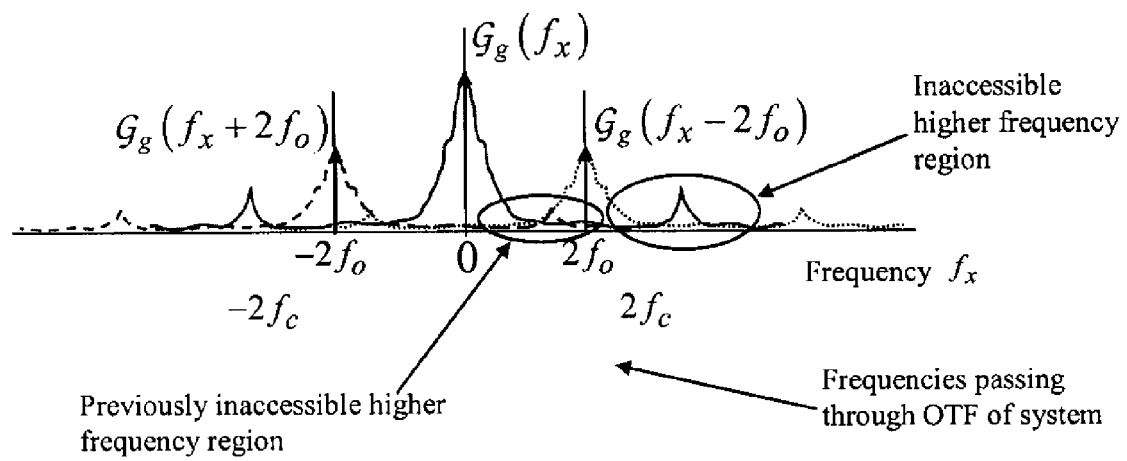
FIG. 1 is a plot showing the visualization of a structured illumination image in the Fourier domain.

Preferred embodiments of the present invention will now be set forth in detail with reference to the drawings, in which like reference numerals refer to like elements or steps throughout.

First, superresolution with sinusoidal illumination in the incoherent case will be considered. Here we assume interaction for light absorption and emission linear in intensity. We demonstrate the case of incoherent illumination such as a metal halide lamp and incoherent fluorescent emission. The sinusoidal pattern is produced by a grating in the illumination path.

The phase estimation analysis which follows is also applicable to the case where a coherent laser illumination is used to project sinusoidal fringes on a fluorescent object. Our method should also be valid for coherent illumination and coherent imaging which is the case of non-fluorescent objects under coherent laser fringe illumination.

Images are formed in the following manner. Assume a vertical sinusoidal illumination field with a spatial frequency $(f_o, 0)$; where $f_o < f_c$, the coherent cut-off frequency of the system and phase shift $\phi_n$, $$U_s(x,y) = \cos(2\pi f_o x + \phi_n). \tag{1}$$

The intensity of this sinusoidal illumination is $$I_s(x, y) = \frac{1}{2}[1 + \cos(4\pi f_o x + 2\phi_n)]. \tag{2}$$

Depending on the method of illumination, the fringe contrast, m, may be less than unity and we have $$I_s(x, y) = \frac{1}{2}[1 + m\cos(4\pi f_o x + 2\phi_n)]. \tag{3}$$

In most simulations that we have done so far, we set m=1 everywhere, assuming maximum contrast of the sinusoid.

We assume that the illumination and imaging path optical transfer functions (OTFs) are given by $H_1$ and $H_2$ respectively. We assume that they both pass through a single limiting lens giving a common coherent cutoff frequency limit, $f_c$. It should be noted that in the case of a doublepass system where the illumination and imaging takes place using the same lens, $H_2(f_x, f_y) = H_1(-f_x, -f_y)$. N such sinusoidally patterned images of the object are taken, where N≧3. The Fourier transform of the $n^{th}$ image, where n=1, 2, ..., N, is given by:

$$G_n(f_x, f_y) = \mathcal{H}_1(0, 0)\mathcal{H}_2(f_x, f_y)\mathcal{G}_g(f_x, f_y) + \tag{4}$$

$$\frac{m}{2}\mathcal{H}_1(2f_o, 0)e^{i2\phi_n}\mathcal{H}_2(f_x, f_y)\mathcal{G}_g(f_x - 2f_o, f_y) +$$

$$\frac{m}{2}\mathcal{H}_1(-2f_o, 0)e^{-i2\phi_n}\mathcal{H}_2(f_x, f_y)\mathcal{G}_g(f_x + 2f_o, f_y)$$

where $G_g$ is the object Fourier transform. This can be visualized as shown in FIG. 1.

The Fourier transform of each image can be seen to consist of three overlapping replicas of the object Fourier transform—one unshifted copy, $G_g(f_x, f_y)$, and two shifted copies, $G_g(f_x-2f_o,f_y)$ and $G_g(f_x+2f_o,f_y)$. The two shifted versions carry the higher frequencies that would conventionally lie outside the passband of the imaging system.

The superresolved image is reconstructed in the following manner. It is essential to separate these three superimposed replicas of the object Fourier transform in order to utilize the superresolution in the two shifted copies. The N images with different phase shifts in the sinusoidal illumination are used to perform this segregation. If one takes a predefined number of images having equally spaced phase shifts then it is possible to arrive at a closed-form solution. However we cannot use this approach because we are interested in considering randomly introduced phase shifts in the sinusoidal illumination. We separate the three superimposed terms on a pixel-by-pixel basis in the Fourier domain. For each pixel in the N image Fourier transforms, we consider a set of N linear equations given by $$AX=B, \tag{5}$$

where $$A = \begin{bmatrix} \mathcal{H}_1(0,0) & \frac{m}{2}\mathcal{H}_1(2f_o,0)e^{i2\phi_1} & \frac{m}{2}\mathcal{H}_1(-2f_o,0)e^{-i2\phi_1} \\ \mathcal{H}_1(0,0) & \frac{m}{2}\mathcal{H}_1(2f_o,0)e^{i2\phi_2} & \frac{m}{2}\mathcal{H}_1(-2f_o,0)e^{-i2\phi_2} \\ \vdots & \vdots & \vdots \\ \mathcal{H}_1(0,0) & \frac{m}{2}\mathcal{H}_1(2f_o,0)e^{i2\phi_N} & \frac{m}{2}\mathcal{H}_1(-2f_o,0)e^{-i2\phi_N} \end{bmatrix}_{N \times 3}, \tag{6}$$

$$X = \begin{bmatrix} \mathcal{H}_2(f_x, f_y)\mathcal{G}_g(f_x, f_y) \\ \mathcal{H}_2(f_x, f_y)\mathcal{G}_g(f_x - 2f_o, f_y) \\ \mathcal{H}_2(f_x, f_y)\mathcal{G}_g(f_x + 2f_o, f_y) \end{bmatrix}_{3 \times 1}, \tag{7}$$

$$B = \begin{bmatrix} \mathcal{G}_1(f_x, f_y) \\ \mathcal{G}_2(f_x, f_y) \\ \vdots \\ \mathcal{G}_N(f_x, f_y) \end{bmatrix}_{N \times 1}. \tag{8}$$

The matrix of coefficients, A, must be known accurately in order to solve this equation. It includes the optical transfer function, $H_1$ and modulation contrast, m, which are both common to all the images. It also contains the phase shifts, $\phi_n$, which uniquely impart diversity to the N images. Hence the knowledge of $\phi_n$ is critical to the accuracy of the matrix A and the recovery of the three overlapping object Fourier transform replicas. If this phase shift is accurately known, then it is a simple matter of using singular value decomposition and pseudoinverse to invert A in order to recover the unknown overlapping terms in matrix X.

The inverse Fourier transform of the unshifted term, weighted by the imaging OTF, $H_2(f_x,f_y)$, gives an image equivalent to the conventional image taken with uniform illumination. This is treated as one composite image containing low frequencies, $I_{c1}$, to be used later to form a superresolved image, $$I_{c1}(f_x,f_y) = H_2(f_x,f_y)G_g(f_x,f_y). \tag{9}$$

The OTF for this composite image is given by, $$otf_1(f_x,f_y) = H_2(f_x,f_y). \tag{10}$$

The two shifted copies of the object Fourier transform, weighted by the imaging OTF, $H_2(f_x, f_y)$, are moved to their true positions in the spatial frequency domain as $I_1'$ and $I_1''$. The sub-pixel shift is accomplished by Fourier methods, $$I_1'(f_x, f_y) = FT\{IFT[\mathcal{H}_2(f_x, f_y)\mathcal{G}_g(f_x - 2f_o, f_y)] \tag{11}$$
$$\exp[-i2\pi(2f_o)x]\}$$
$$= \mathcal{H}_2(f_x + 2f_o, f_y)\mathcal{G}_g(f_x, f_y)$$

And $$I_1''(f_x, f_y) = FT\{IFT[\mathcal{H}_2(f_x, f_y)\mathcal{G}_g(f_x + 2f_o, f_y)] \tag{12}$$
$$\exp[+i2\pi(2f_o)x]\}$$
$$= \mathcal{H}_2(f_x - 2f_o, f_y)\mathcal{G}_g(f_x, f_y).$$

The two terms, $I_1'$ and $I_1''$, are now added so as to form a composite image, $I_{c2}$, which contains high superresolution frequencies in one direction in Fourier space, $$I_{c2}(f_x, f_y) = [H_2(f_x+2f_o, f_y) + H_2(f_x-2f_o, f_y)]G_g(f_x, f_y). \quad (13)$$

$I_{c2}$ will also be used later, along with $I_{c1}$, to form a single superresolved image. The OTF for $I_{c2}$ is given by, $$otf_2(f_x, f_y) = [H_2(f_x+2f_o, f_y) + H_2(f_x-2f_o, f_y)]. \quad (14)$$

Similarly, this is repeated with the orientation of the sinusoidal illumination rotated by, say, 60° and 120°, to obtain four more composite images, $I_{c3}$ and $I_{c5}$, which provide low frequency information, and $I_{c4}$ and $I_{c6}$, which provide high frequency superresolution along the 60° and 120° orientations in the Fourier domain. Corresponding OTFs, are also obtained for the these images as $otf_3$, $otf_4$, $otf_5$ and $otf_6$.

Now these six composite images must be combined with appropriate weighting and OTF compensation to obtain the reconstructed image which has superresolution in all directions in the Fourier domain. We use the following filter to OTF compensate and combine these six composite images appropriately to obtain the reconstructed superresolved image $$I_{rec}(x, y) = IFT\left\{ \sum_{i=1}^{M} \left[ \frac{I_{ci}(f_x, f_y) otf_i^*(f_x, f_y) \times \frac{\Phi_O(f_x, f_y)}{\Phi_{Ni}}}{c + \sum_{j=1}^{M} |otf_j(f_x, f_y)|^2 \times \frac{\Phi_O(f_x, f_y)}{\Phi_{Nj}}} \right] \right\} \quad (15)$$

where M is the number of composite images, $I_{ci}$, that go into forming the reconstruction. In the present case with 3 orientations we have M=6, each orientation of the sinusoidal illumination contributing 2 composite images—one conventional and one with superresolution in one direction in Fourier space. The term $\Phi_O$ is the object power spectrum. This is estimated from the conventional image using a generalized model for the object power spectrum. We assume that the object is identical in all the composite images; hence $\Phi_O$ is the same for all $I_{ci}$ in this filter. The term $\Phi_{Ni}$ is the power spectrum of the noise in each composite image; hence it is separately calculated for each $I_{ci}$. The constant c may be used subjectively to weight the combination to give an image that might appear better to the observer. In our simulations we set c=1, which is the least square solution. Next we will show how to estimate the phase shifts when they are unknown.

The phase shift of the sinusoidal illumination in each image can be estimated a posteriori in several ways. One such way is to average the image along the sinusoid fringe direction and then fit an ideal sinusoid to it. But variations in the object intensity perturb this estimation. It is also difficult to average the image along the sinusoid if its orientation is not exactly parallel to one of the pixel directions on the CCD, since the interpolation of the values of pixels parallel to the orientation of the sinusoid introduces error in the phase-shift estimate. This technique also poses the difficulty that when the frequency of the sinusoidal illumination increases, the term $H_1(2f_o,0) H_2(2f_o,0)$ typically reduces its contrast and the reconstructed image becomes increasingly noisy. In this case simply curve fitting the averaged sinusoid no longer provides an accurate estimate of the phase shift.

Another technique is to vary the estimates of the phase shifts in such a way as to minimize the residual sinusoidal patterned artifacts in the reconstructed image. This method is somewhat time consuming and might need good initial estimates of the phase shift to avoid stagnation.

In our approach, we take the Fourier transform of a sinusoidally illuminated image. In the Fourier domain we extract the phase of the shifted impulse arising from the spatial frequency of the sinusoidal illumination. The Fourier transform of the intensity of a vertical fringe shows three impulses located at (0,0), $(2f_o,0)$ and $(-2f_o,0)$. Therefore, when the image is illuminated by this sinusoid consider the value of its Fourier transform, $G_n$, given by Eq. (4) at $(2f_o,0)$, $$G_n(2f_o, 0) = \mathcal{H}_1(0, 0)\mathcal{H}_2(2f_o, 0)\mathcal{G}_g(2f_o, 0) + \quad (16)$$
$$e^{i2\phi_n}\frac{m}{2}\mathcal{H}_1(2f_o, 0)\mathcal{H}_2(2f_o, 0)\mathcal{G}_g(0, 0) +$$
$$e^{-i2\phi_n}\frac{m}{2}\mathcal{H}_1(-2f_o, 0)\mathcal{H}_2(2f_o, 0)\mathcal{G}_g(4f_o, 0).$$

We note that in the above equation the first term, $H_1(0,0) H_2(2f_o,0)G_g(2f_o,0)$, is much smaller than the second term because $|G_g(2f_o,0)| \ll G_g(0,0)$ for an extended object. Similarly the third term, $$e^{-i2\phi_n}\frac{m}{2}\mathcal{H}_1(-2f_o, 0)\mathcal{H}_2(2f_o, 0)\mathcal{G}_g(4f_o, 0),$$

proportional to $|G_g(4f_o,0)| \ll G_g(0,0)$, is small. Hence the first and third terms have a relatively small contribution to the Fourier transform of the image at this location as long as the frequency $f_o$ is not too low.

The most significant contribution comes from the second term, $$e^{i2\phi_n}\frac{m}{2}\mathcal{H}_1(2f_o, 0)\mathcal{H}_2(2f_o, 0)\mathcal{G}_g(0, 0).$$

Also $G_g(0,0)$ and m are real valued, as are $H_1(2f_o,0)$ and $H_2(2f_o,0)$ when we use well corrected optics with no aberrations. Then the only phase contribution to this equation comes from $e^{i2\phi_n}$. Hence the phase shift of the sinusoidal illumination is approximately the phase of this peak in the Fourier transform of the image, $$\phi_n = \frac{1}{2}\tan^{-1}\left\{\frac{imag[G_n(2f_o, 0)]}{real[G_n(2f_o, 0)]}\right\}. \quad (17)$$

Here the arctangent is computed using the a tan 2 function in Matlab where the resulting phase lies between $-\pi$ to $\pi$. If the sinusoidal illumination intensity has a generalized spatial frequency $(2f_{ox}, 2f_{oy})$ for a rotated fringe pattern, then the phase shift can be estimated as $$\phi_n = \frac{1}{2}\tan^{-1}\left\{\frac{imag[G_n(2f_{ox}, 2f_{oy})]}{real[G_n(2f_{ox}, 2f_{oy})]}\right\}. \quad (18)$$

It must be noted that if the spatial frequency of the sinusoidal illumination is very low, then the first and second terms in Eq. (16) become non-negligible. Their contribution then cannot be ignored and this phase estimate might then be inaccurate. If the illumination and imaging optical transfer functions have aberrations, then there might be some inaccuracy due to phase contributions from the aberrations. Also, at very high spatial frequencies of the sinusoidal illumination approaching cutoff frequency, the value of $H_1(2f_o,0)H_2(2f_o,0)$ will attenuate the sinusoid and lower its contrast substantially, decreasing the accuracy of the phase estimate.

Here we also note that in the case of a doublepass system, where the illumination and imaging use the same lens and $H_2(f_x,f_y)=H_1(-f_x,f_y)$, odd aberrations cancel out and even aberrations double in value affecting the phase-shift estimate.

Figure 2:
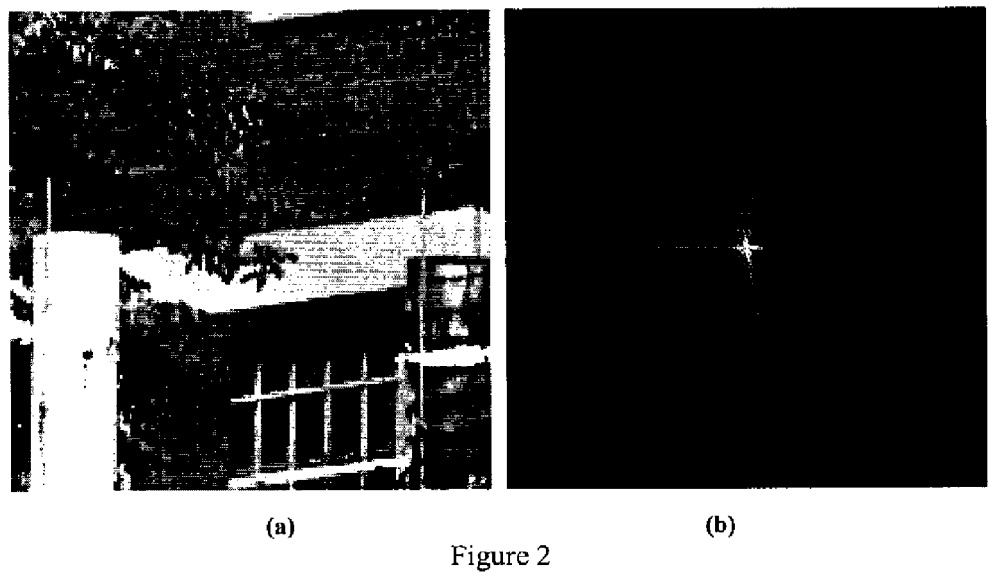
FIG. 2 shows a pristine object (a) and its Fourier transform (b)

To demonstrate this approach to sinusoidal phase-shift estimation, we simulated an incoherent sinusoidal illumination setup with three orientations of the sinusoid, rotated 0°, 120° and 240°, and an incoherent image with no aberrations. We use a pristine object with a Fourier transform shown in FIG. 2.

The accuracy of our phase-shift estimates varies with each orientation because when a significant component of the unshifted object Fourier transform overlaps with the peak of the shifted object Fourier transform, the contribution from the first term increases, decreasing the accuracy of the estimated phase. Our simulation object has distinct horizontal and vertical streaks in the Fourier domain, as seen in FIG. 2(b) contributing to the variation in overlap with the orientation of the sinusoidal illumination of our object.

Figure 3:
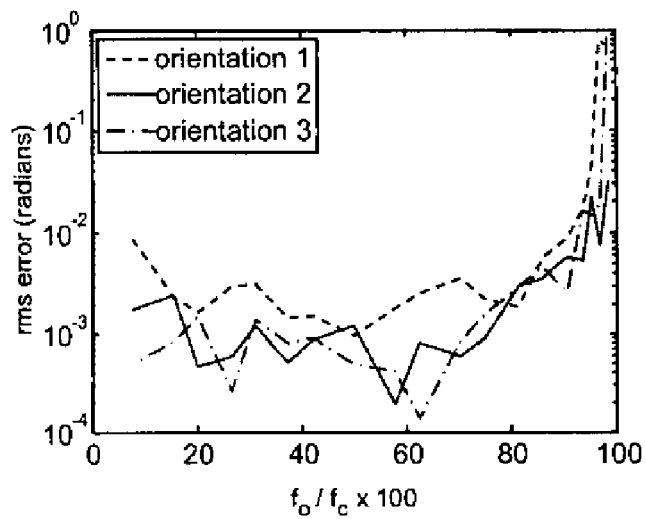
FIG. 3 is a plot of RMS error in phase shift estimate versus spatial frequency of sinusoidal illumination, $f_o/f_c$ with no noise.
Figure 4:
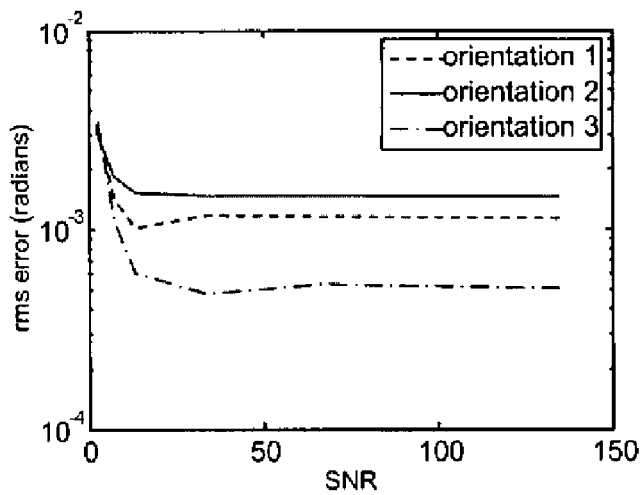
FIG. 4 is a plot of RMS error in phase shift estimate versus SNR for sinusoidal illumination with $f_o = 50\% f_c$.
Figure 5:
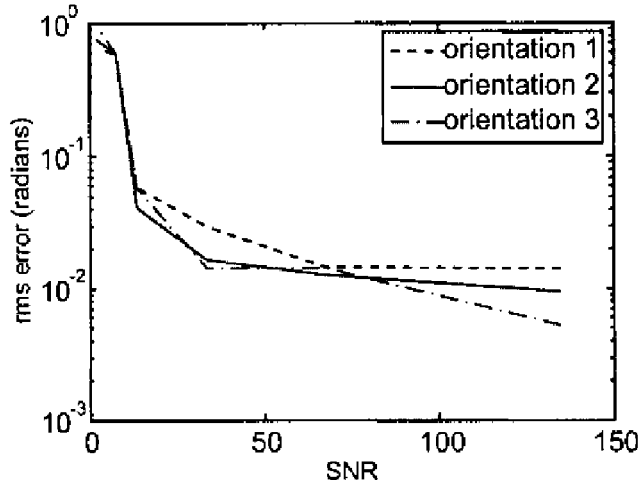
FIG. 5 is a plot of RMS error in phase shift estimate versus SNR for sinusoidal illumination with $f_o = 91\% f_c$

The accuracy of our estimates also varies with the spatial frequency of the sinusoidal illumination. As shown in FIG. 3, we achieved accuracy better than $6\times10^{-3}$ radians RMS for frequencies, $f_o$, between 15%-85% of the coherent cutoff frequency, $f_c$. As expected, the error in the estimate increases at higher spatial frequencies of the sinusoidal illumination due to the reduction in the contrast of the sinusoidal illumination proportional to $H_1(2f_o,0)H_2(2f_o,0)$. At lower spatial frequencies of the sinusoid, error in the estimate increases because the value of the first term in Eq. (16) increases. FIG. 4 shows the plot of RMS error in our estimates for different values of SNR when $f_o=50\% f_c$. The accuracy in the estimates for the worst case was better than $1.5\times10^{-3}$ radians RMS for moderate SNR. The error in our estimates increased up to $4\times10^{-3}$ radians RMS for SNR in the range 2-7. FIG. 5 shows the same for a sinusoidal illumination frequency of $f_o=91\% f_c$. Here the accuracy was better than $3\times10^{-2}$ radians for moderate to high SNR. This is several times worse than for the previous case, but we have observed that in this frequency range even an error up to $10^{-2}$ radians gives us images having no noticeable artifacts. The error increased up to 0.95 radians for lower SNR in the range 2-13 since for these levels of SNR the reduced contrast of the sinusoid is comparable to the noise floor. This range of error would definitely give rise to artifacts in the reconstructed image.

Figure 6:
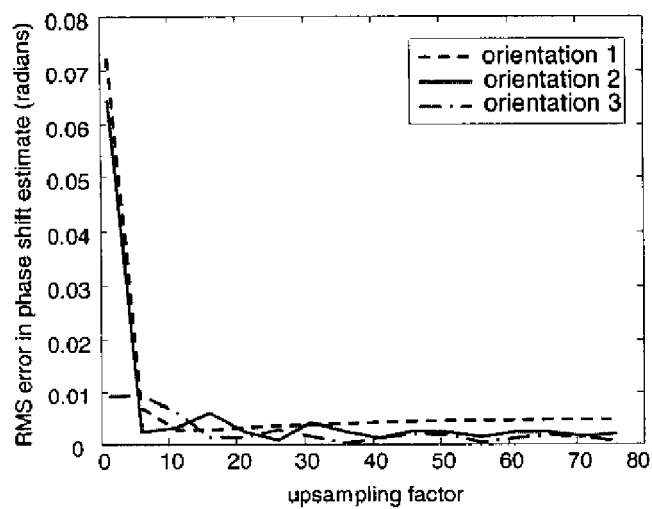
FIG. 6 is a plot of RMS error in phase shift estimate versus upsampling factor; $f_o = 50\% f_c$; SNR=15.5.

Our simulations indicate that upsampling $G_n(2f_o,0)$, the value of the image Fourier transform at $(2f_o,0)$, improves the accuracy of the phase-shift estimate. We tried upsampling $G_n(2f_o,0)$ with factors up to 76 and estimated the phase shift for each upsampled condition. We look at the RMS error in the phase-shift estimate when compared with the known phase shift introduced in the simulation. The RMS error in the phase-shift estimate versus the upsampling factor of the sinusoidal illumination obtained for different orientations of the sinusoidal illumination is plotted in FIG. 6. The RMS error drops sharply for upsampling factors up to 20 or 30 and then the curve becomes flat. This trend in the curve is maintained even in the presence of substantial noise. The curve shown in FIG. 6 used images with Gaussian noise having SNR 15.5. This graph has been plotted for a sinusoid at 50% of cutoff frequency. We tried frequencies up to 93% of cutoff and this trend of improvement in phase shift estimates for upsampling factors up to 20-30 is seen even at higher frequencies of the sinusoidal illumination.

It should be noted here that care needs to be taken while upsampling the Fourier transform of the image. For perfectly vertical or horizontal sinusoidal illumination patterns the peaks from the sinusoidal illumination in the Fourier domain lie exactly on the $f_x$ or $f_y$ axes. Upsampling methods may exacerbate the ringing effect from the edges of the image in the Fourier domain and introduce error in the upsampled phase shift estimate. Therefore, from this simulation onwards, we use a sinusoidal illumination that is neither exactly vertical nor horizontal. We now use sinusoidal illumination that makes roughly 11°, 131° and 251° angles with respect to the vertical $f_y$ axis instead of the 0°, 120° and 240° orientations we used before.

Images are reconstructed in the following manner. These phase-shift estimates can be used to recover the three copies of the object Fourier transform from the N images using singular value decomposition and pseudoinverse. The reconstructed image is formed by appropriate weighting and superposition of the retrieved object spectra as shown in Eq. (15).

Figure 7:
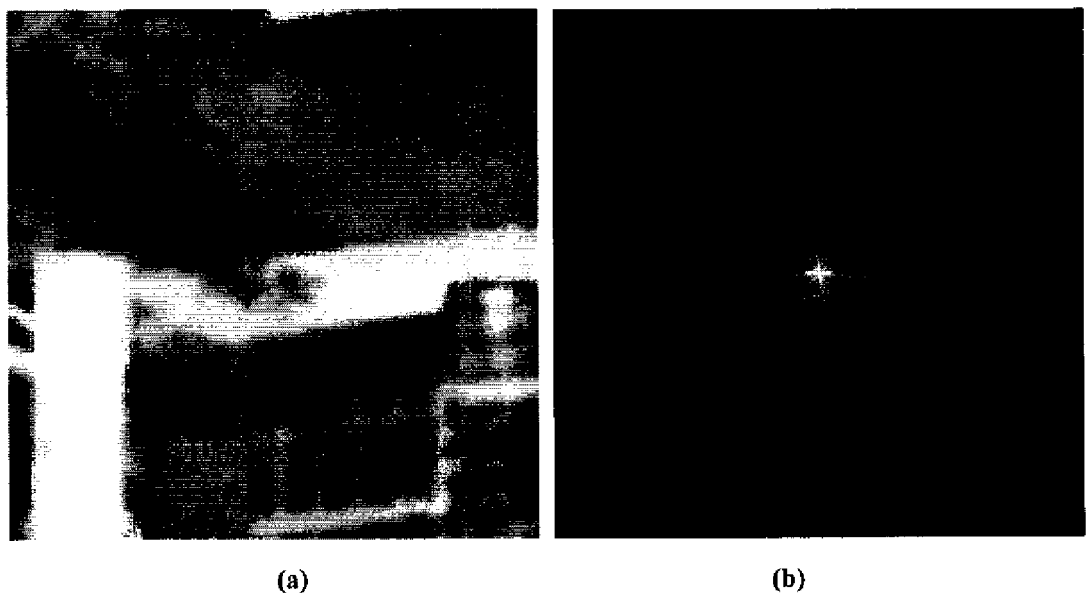
FIG. 7 shows a conventional image (a) and its Fourier transform (b); no noise.
Figure 8:
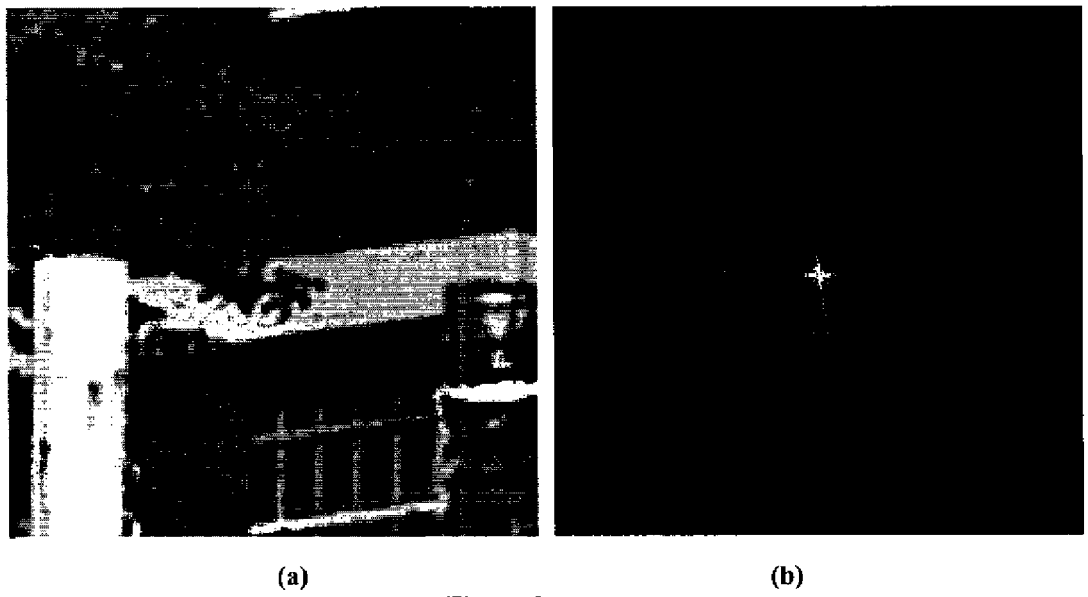
FIG. 8 shows a deconvolved conventional image (a) and its Fourier transform (b); no noise.
Figure 9:
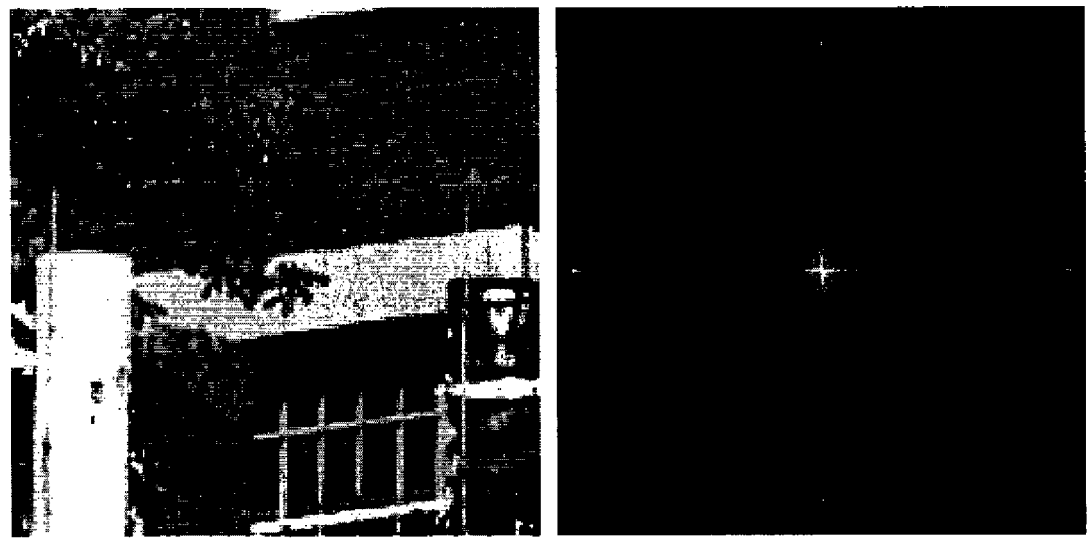
FIG. 9 shows an image with 91% superresolution (a) and its Fourier transform (b); no noise; known phase shifts.

FIG. 7 shows a simulated conventional image taken with uniform illumination and its Fourier transform. FIG. 8 is the OTF-compensated version of the conventional image and its Fourier transform. FIG. 9 is the OTF-compensated superresolved image, having 91% superresolution, and its Fourier transform. There is no added noise in any of these images and the superresolution processing for these images uses known phase shifts.

Figure 10:
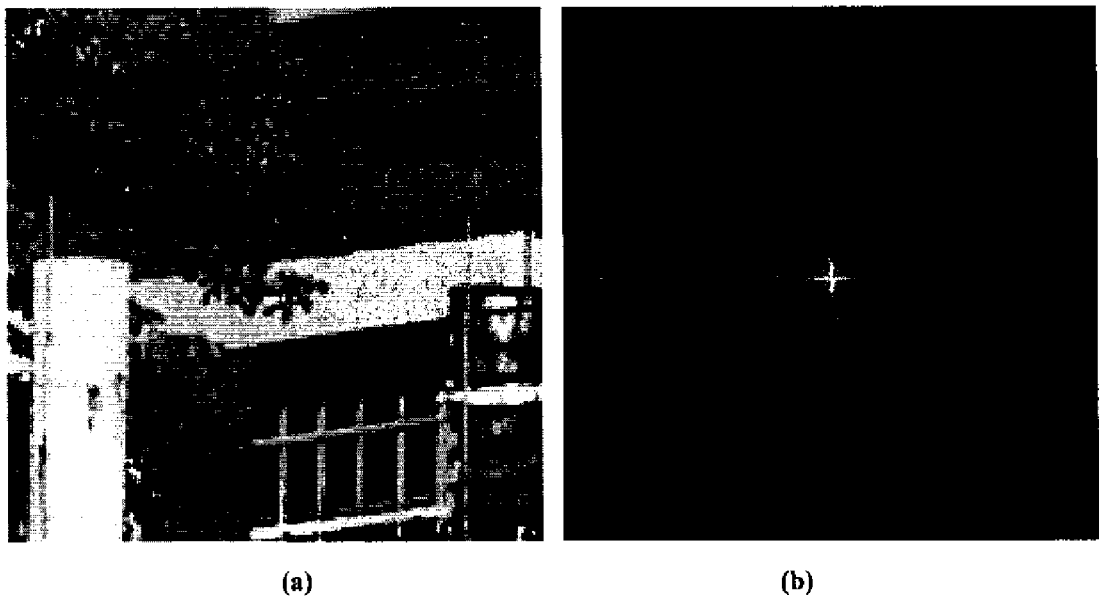
FIG. 10 shows an image with 75% superresolution (a) and its Fourier transform (b); no noise, using estimated phase shifts.

The results for image reconstruction using estimated phase shifts will now be described. FIG. 10 is a reconstruction with 75% superresolution and its Fourier transform. It has been obtained from noise-free sinusoidally patterned images using phase shift estimates that were obtained with 36 times upsampling. We saw no significant artifacts such as residual sinusoidal patterns in most reconstructed images. This confirms that our phase shift estimate is accurate enough to provide artifact free reconstruction.

Figure 11:
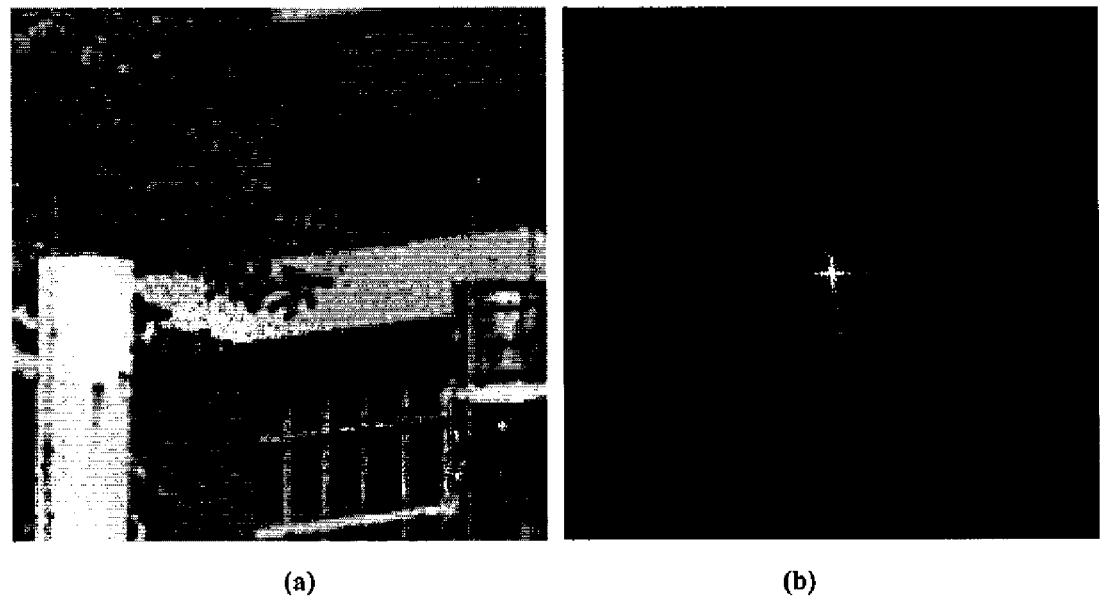
FIG. 11 shows an averaged sum of 2 images with 50% superresolution (a) and its Fourier transform (b); SNR 125, known phase shifts.

The results for image reconstruction in the presence of noise will now be discussed. The presence of noise in the image deteriorates its quality. Averaging multiple images helps improve such noisy images. FIG. 11 shows a reconstruction with 50% superresolution and its Fourier transform. This image has made from sinusoidally patterned images with SNR 125 using known phase shifts. Estimated phase shifts also provide good reconstructions, but here we show reconstructions using known phase shifts to particularly emphasize the effect of noise on the reconstruction. We have averaged two superresolved images to obtain good signal in this image.

Figure 12:
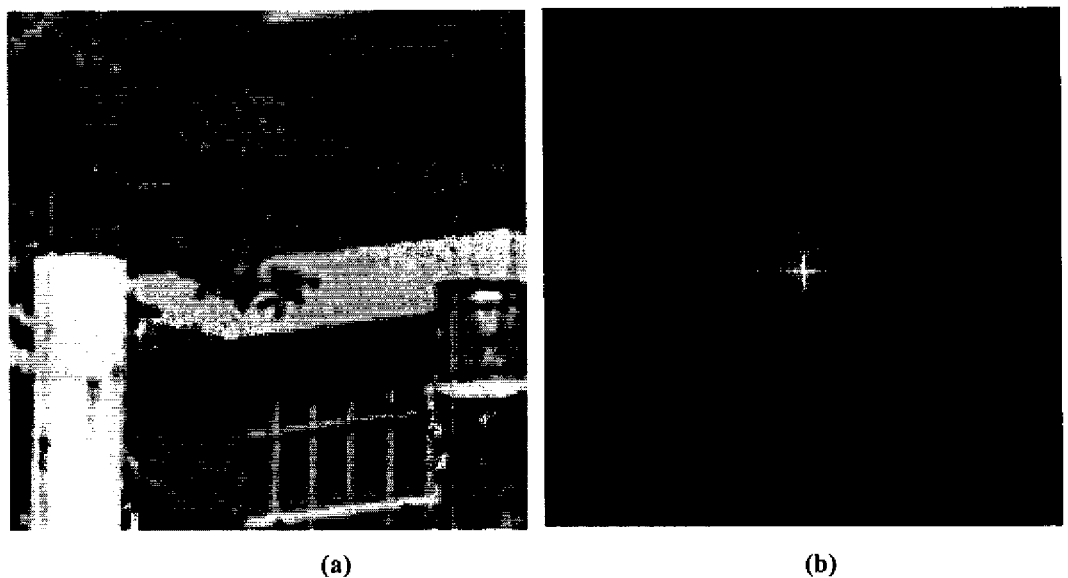
FIG. 12 shows an averaged sum of 20 images with 75% superresolution (a) and its Fourier transform (b); SNR 125; known phase shifts.

At higher frequencies of sinusoidal illumination, however, the noise in the image is very close to the reduced contrast of the sinusoidal illumination. Therefore the useful superresolution signal in noisy images tends to be very weak and we need to average several images to get good superresolution. FIG. 12 contains an averaged sum of 20 reconstructions, each having 75% superresolution and its Fourier transform.

Very similar processing is involved for obtaining axial sectioning in such images. This demonstrates our ability to use sinusoidally patterned illumination to obtain artifact-free superresolution with no prior knowledge of randomly introduced phase shifts. This will later be used to implement superresolution in moving objects by using image registration and phase-shift estimation.

The setup used will now be described. We used a fluorescence microscope (Olympus IX51) with a 4× objective and a reduced NA of 0.047 to image a FluoCells® prepared slide (F-24630 by Molecular Probes) containing a section of mouse kidney cells stained with green fluorescent Alexa Fluor® 488 (excitation—495 nm/emission—519 nm) for elements in glomeruli and convoluted tubules. We used a FITC filter cube (excitation—494 nm/emission—518 nm) for the fluorescence imaging. The resolution in the image was 5.5 µm. An OptiGrid (Qioptiq Imaging Solutions, Inc.) attachment containing a grating in the plane of the field stop of the microscope was used to project an incoherent sinusoidal patterned illumination with a period of about 17.1 µm on the specimen. The grating was moved in precisely known steps by a calibrated precision translation stage to introduce known phase shifts in the sinusoidal illumination on the object. We took multiple images of the specimen with different phase steps of the sinusoidal illumination.

For stationary images, the present embodiment will be compared to calibrated readings. We now consider a set of N=3 images where the phase of the horizontal fringe illumination was varied in pre-calibrated steps—0°, 120° and 240°. Such calibrations are usually relative and hence the introduced phase shifts are relative to the first image. We estimate the absolute phase-shift of the sinusoid in each image as described above using the phase at the location of the shifted peak in the Fourier transform of each sinusoidally patterned image. This estimated absolute and relative phase shifts are compared with the phase shift readings from the calibrated precision translation stage. The results are shown in Table 1.

TABLE 1

Difference between relative phase shift calibrated readings and relative phase shift estimates

|  | Image 1 (radians) | Image 2 (radians) | Image 3 (radians) |
|---|---|---|---|
| Relative phase shift calibrated reading | 0 | 120.0 | 240.0 |
| Phase shift estimate | −85.6 | 37.7 | 159.4 |
| Relative estimate | 0 | 123.4 | 245.0 |
| Difference between calibrated reading and relative estimate | 0 | 3.4 | 5 |

It is necessary to know the absolute phase shifts in the final processing of these images. The N sinusoidally patterned images are used to solve for the three overlapping terms in each orientation of the sinusoidal fringe illumination: $H_2(f_x,f_y)G_g(f_x,f_y)$, $H_2(f_x,f_y)G_g(f_x-2f_o,f_y)$ and $H_2(f_x,f_y)G_g(f_x+2f_o,f_y)$. If the absolute phase-shifts are unknown but relative phase-shifts are known, and if they are relative to the first of the N images for each orientation, then we would actually have solved for $H_2(f_x,f_y)G_g(f_x,f_y)$, $H_2(f_x,f_y)G_g(f_x-2f_o,f_y)e^{i2\phi_1}$ and $H_2(f_x,f_y)G_g(f_x+2f_o,f_y)e^{-i2\phi_1}$. Thus the shifted terms would have a phase which is offset by the phase of the first image. Therefore, each composite image with superresolution in one direction would contain this phase offset. Also, we will have three different phase terms in the composite images obtained from the three orientations of the sinusoidal illumination. These phase terms would be present through the combination and OTF compensation of these composite images and hence would introduce errors in their combination. The different phase terms would affect the real and imaginary contributions of the Fourier transform of the composite images in a different manner for every orientation. Therefore the combination of these terms from different orientations would be erroneous. This can be avoided by somehow estimating the remnant phase shift for each orientation and compensating for it in each orientation before proceeding to the OTF compensation and combination of multiple images. This complication in the combination of sub-images does not arise at all when we use our absolute phase-shift estimates.

Figure 13:
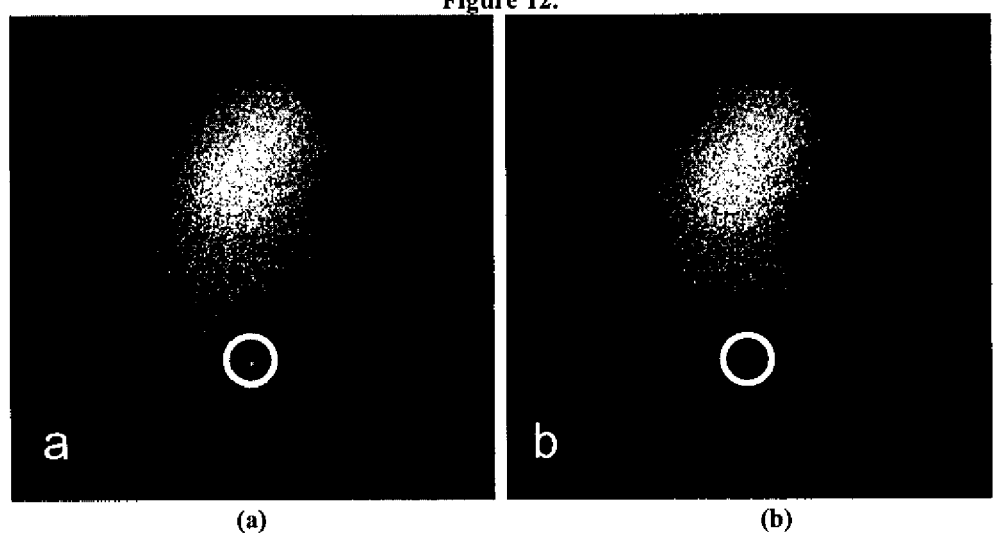
FIG. 13 shows a Fourier transform of recovered shifted object Fourier transform, in which (a) shows a residual peak (encircled) when calibrated phase shift readings were used, but (b) shows a negligible residual peak (encircled) when our phase shift estimates were used.

The bias-subtracted root mean squared difference between the relative values of our estimates and the calibrated readings is about 2.1 degrees. The implication of this difference is clear when we use the calibrated phase-shift readings versus our estimated phases to separate the three overlapping copies of the object Fourier transform and reconstruct the superresolved image. In both cases we see no visible residual fringe artifacts in the reconstruction. But the difference is more distinct if we look at the recovered shifted object Fourier transform, $H_2(f_x,f_y)G_g(f_x-2f_o,f_y)$. As seen in FIG. 13a the recovered shifted object Fourier transform, $H_2(f_x,f_y)G_g(f_x-2f_o,f_y)$, obtained by using the calibrated phases shows some residual peak. The recovered Fourier transform shown in FIG. 13b obtained by using our estimated phase shifts has negligible residual peak as shown in Table 2 suggesting that our estimated phase shifts are more accurate than the calibrated phase shifts.

TABLE 2

Ratio of residual peak to average in the area around it and value of the residual peak normalized with respect to the value of the actual peak for segregated object Fourier transforms obtained by using calibrated versus estimated phase shifts.

|  | Ratio of residual peak to average area around it | Normalized value of residual peak |
|---|---|---|
| Using calibrated phase shift readings | 190.9 | 0.0281 |
| Using estimated phase shifts | 83.7 | 0.0031 |

The complete absence of this residual peak indicates perfect separation of the three overlapping object Fourier transforms. If not completely removed, this residual peak eventually contributes to a residual fringe artifact in the superresolved image. Hence the neglible residual peak in the recovered Fourier transform from our phase estimate indicates better separation of the overlapping object Fourier transforms and will reduce the likelihood of fringe artifacts in the reconstructed image.

Figure 14:
FIG. 14 shows a conventional image.
Figure 15:
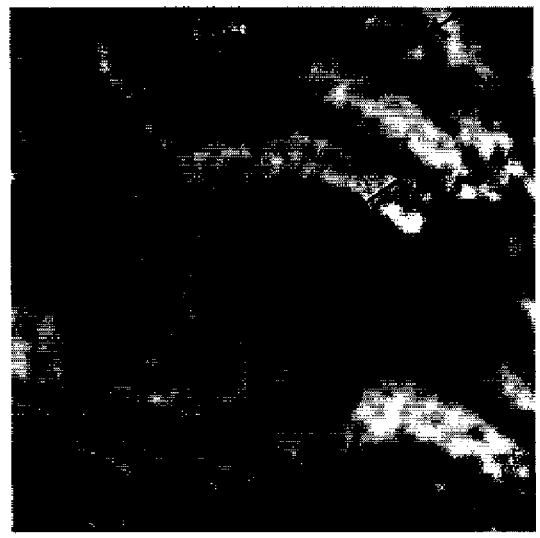
FIG. 15 shows a conventional Image with OTF compensation.
Figure 16:
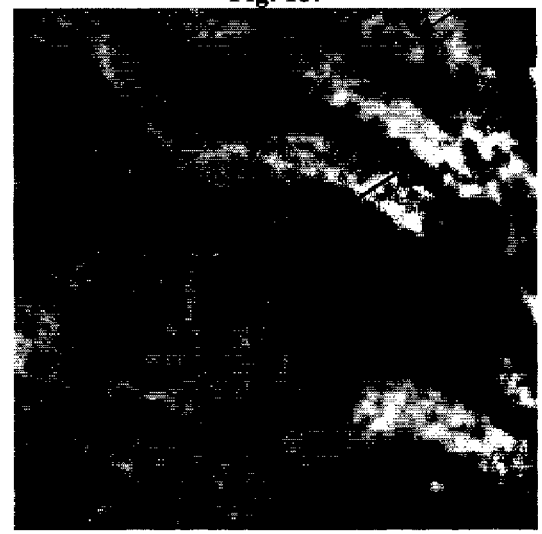
FIG. 16 shows an image with 32.2% superresolution obtained using our estimated phase shifts.

FIG. 14 shows the conventional uniformly illuminated image and FIG. 15 is its OTF-compensated version. FIG. 16 shows the image with 32.2% superresolution, reconstructed using our estimated phase shifts. Here we have superresolution along the vertical axis only, because this reconstruction includes only images with a horizontal sinusoidal fringe illumination. The black arrows point to clear line features which can be distinctly seen in the superresolved image, but are indistinct and blurred in the conventional image. The images shown here are zoomed-in portions of larger images. The constant in the combination filter is chosen as c=1.

Superresolution for moving objects will now be discussed. Our eventual goal is to estimate the phase shifts in images of objects that have translational motion between successive sinusoidally illuminated frames. To test this we allowed the sinusoidal fringe pattern to stay stationary and moved the object stage in the x-y plane to replicate basic translational object motion, taking six randomly translated images. We registered each of the six sinusoidally illuminated images with a conventional, uniformly illuminated image as reference. We used a normalized cross-correlation algorithm with non-linear optimization which registers to a precision of about 0.01 pixel. The registered images have aligned the sample, but the sinusoidal illumination on it is effectively shifted randomly.

Figure 17:
FIG. 17 shows a conventional image taken with uniform illumination.
Figure 18:
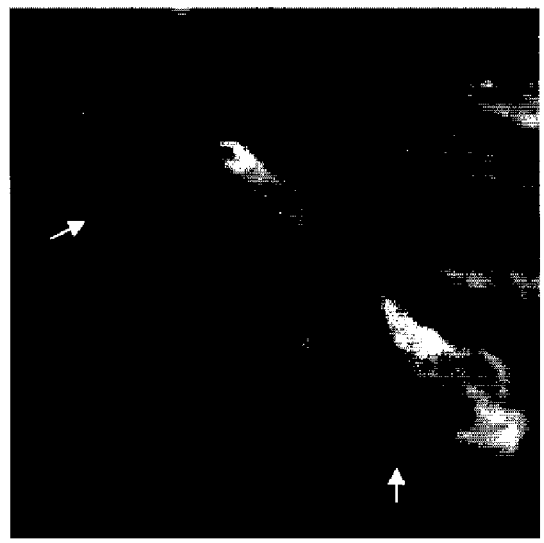
FIG. 18 shows an OTF compensated conventional image taken with uniform illumination.
Figure 19:
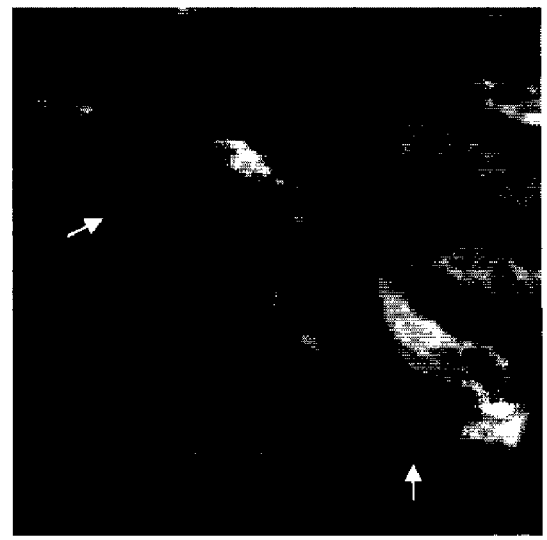
FIG. 19 shows an image with 32.2% superresolution reconstructed after registering sinusoidally illuminated images and estimating phase shifts.

We repeat our phase-shift estimation on these registered images. FIG. 17 shows the conventional image taken with uniform illumination and FIG. 18 is its OTF-compensated version. FIG. 19 shows the image with 32.2% superresolution, reconstructed using the estimated phase shifts. The constant in the combination filter is chosen as c=1. The reconstruction shows no residual sinusoidal patterned artifacts. Here also we have superresolution along the vertical y axis only, because this reconstruction includes only images with a horizontal sinusoidal illumination. We will include other orientations of the sinusoidal illuminations in our work in future. White arrows point to line features in both images which are very distinct in the superresolved image but very blurred in the conventional image.

Very similar processing is involved for obtaining axial sectioning in such images. This demonstrates our ability to use sinusoidally patterned illumination to obtain artifact-free superresolution and axial sectioning in moving objects by using image registration and phase shift estimation.

Another preferred embodiment will now be disclosed, using coherent structured illumination. We consider the case where the illumination is from a laser source and the object has no innate fluorescence. Therefore, the image is completely coherent. The field distribution of the illumination pattern incident on the object in a doublepass system is given by, $$U_{illum}(x,y) = \cos(2\pi f_o x + \phi_n) * h_1(x,y). \tag{19}$$

If the object is placed at the back focal plane of the lens, the fringe illumination will be incident on it. The object and illumination fields will multiply to produce the effective reflected field. And the effective object field, is given by $$U_s(x,y) = U_{illum}(x,y) U_g(x,y). \tag{20}$$

Using Eq. (19), the Fourier transform of the above equation gives us $$G_s(f_x, f_y) = FT\{[\cos(2\pi f_o x + \phi_n) * h_1(x,y)] U_g(x,y)\}, \tag{21}$$

$$G_s(f_x, f_y) = \tag{22}$$

$$\frac{1}{2}\{H_1(f_x, f_y)[e^{i\phi_n}\delta(f_x - f_o) + e^{-i\phi_n}\delta(f_x + f_o)]\} * G_g(f_x, f_y).$$

where $G_g$ is the Fourier transform of $U_g$. This gives us $$G_s(f_x, f_y) = \tag{23}$$

$$\frac{1}{2}[e^{i\phi_n}H_1(f_o, 0)\delta(f_x - f_o) + e^{-i\phi_n}H_1(-f_o, 0)\delta(f_x + f_o)] * G_g(f_x, f_y),$$

$$G_s(f_x, f_y) = \tag{24}$$

$$\frac{1}{2}e^{i\phi_n}H_1(f_o, 0)G_g(f_x - f_o, f_y) + \frac{1}{2}e^{-i\phi_n}H_1(-f_o, 0)G_g(f_x + f_o, f_y).$$

The Fourier spectrum of the image of a sinusoidally illuminated object is given by, $$G_{is}(f_x, f_y) = H_2(f_x, f_y) G_s(f_x, f_y). \tag{25}$$

Substituting Eq. (24) in Eq. (25), we get $$G_{is}(f_x, f_y) = H_2(f_x, f_y)\left[\frac{1}{2}e^{i\phi_n}H_1(f_o, 0)G_g(f_x - f_o, f_y) + \right. \tag{26}$$

$$\left.\frac{1}{2}e^{-i\phi_n}H_1(-f_o, 0)G_g(f_g + f_o, f_y)\right]$$

The imaging equation is given as $$I_{is} = |h_2 * U_s|^2. \tag{27}$$

And its Fourier transform is $$G_{is} = (H_2 G_s) \circledast (H_2 G_s), \tag{28}$$

$$G_{is} = G_{is} \circledast G_{is}, \tag{29}$$

$$\mathcal{G}_{is}(f_x, f_y) = \int_\infty \int G_{is}(\xi, \eta) G_{is}^*(\xi - f_x, \eta - f_y) d\xi d\eta. \tag{30}$$

Substituting equation (26) in (30) we get $$\mathcal{G}_{is}(f_x, f_y) = \frac{1}{4}\int_\infty \int (\{H_2(\xi, \eta)[e^{i\phi_n}H_1(f_o, 0)G_g(\xi - f_o, \eta) + e^{-i\phi_n}H_1(-f_o, 0)G_g(\xi + f_o, \eta)]\} \times \tag{31}$$

$$\{H_2(\xi - f_x, \eta - f_y)[e^{i\phi_n}H_1(f_o, 0)G_g(\xi - f_o - f_x, \eta - f_y) + e^{-i\phi_n}H_1(-f_o, 0)G_g(\xi + f_o - f_x, n - f_y)]\}^*)d\xi d\eta,$$

$$\mathcal{G}_{is}(f_x, f_y) = \frac{1}{4}|H_1(f_o, 0)|^2 \int_\infty \int H_2(\xi, \eta)H_2^*(\xi - f_x, \eta - f_y) \times G_g(\xi - f_o, \eta)G_g^*(\xi - f_o - f_x, \eta - f_y)d\xi d\eta + \tag{32}$$

$$\frac{1}{4}|H_1(-f_o, 0)|^2 \int_\infty \int H_2(\xi, \eta)H_2^*(\xi - f_x, \eta - f_y) \times G_g(\xi + f_o, \eta)G_g^*(\xi + f_o - f_x, \eta - f_y)d\xi d\eta +$$

$$\frac{e^{i2\phi_n}}{4}H_1(f_o, 0)H_1^*(-f_o, 0) \int_\infty \int H_2(\xi, \eta)H_2^*(\xi - f_x, \eta - f_y) \times G_g(\xi - f_o, \eta)G_g^*(\xi + f_o - f_x, \eta - f_y)d\xi d\eta +$$

$$\frac{e^{-i2\phi_n}}{4}H_1(-f_o, 0)H_1^*(f_o, 0) \int_\infty \int H_2(\xi, \eta)H_2^*(\xi - f_x, \eta - f_y) \times G_g(\xi + f_o, \eta)G_g^*(\xi - f_o - f_x, \eta - f_y)d\xi d\eta.$$

Now if we assume a symmetric pupil, then we have, $$|H_1(f_o, 0)| = |H_1(-f_o, 0)|. \tag{33}$$

Therefore, Eq. (32) is now written as, $$\mathcal{G}_{is}(f_x, f_y) = \tag{34}$$

$$\frac{1}{4}|H_1(f_o, 0)|^2 \left[\int_\infty \int H_2(\xi, \eta)H_2^*(\xi - f_x, \eta - f_y) \times G_g(\xi - f_o, \eta)\right.$$

$$G_g^*(\xi - f_o - f_x, \eta - f_y)d\xi d\eta +$$

$$\int_\infty \int H_2(\xi, \eta)H_2^*(\xi - f_x, \eta - f_y) \times G_g(\xi + f_o, \eta)$$

-continued $$G_g^*(\xi + f_o - f_x, \eta - f_y)d\xi d\eta \Big] +$$

$$\frac{e^{i2\phi_n}}{4}H_1(f_o, 0)H_1^*(-f_o, 0)\int\int_\infty H_2(\xi, \eta)H_2^*(\xi - f_x, \eta - f_y) \times$$

$$G_g(\xi - f_o, \eta)G_g^*(\xi + f_o - f_x, \eta - f_y)d\xi d\eta +$$

$$\frac{e^{-i2\phi_n}}{4}H_1(-f_o, 0)H_1^*(f_o, 0)\int\int_\infty H_2(\xi, \eta)H_2^*(\xi - f_x, \eta - f_y) \times$$

$$G_g(\xi + f_o, \eta)G_g^*(\xi - f_o - f_x, \eta - f_y)d\xi d\eta.$$

In equation (34) we see that term 1 is a sum of the autocorrelations of $H_2(f_x,f_y)G_g(f_x-f_o,f_y)$ and $H_2(f_x,f_y)G_g(f_x+f_o, f_y)$. Both the autocorrelations peak at zero spatial frequency. Therefore, they appear summed and centered around zero as the origin.

Term 2 is the cross correlation of $H_2(f_x,f_y)G_g(f_x-f_o,f_y)$ with $H_2(f_x,f_y)G_g(f_x+f_o,f_y)$. This term is maximum at $f_x=2f_o$. Similarly, term 3 is the cross correlation of $H_2(f_x,f_y)G_g(f_x+f_o,f_y)$ with $H_2(f_x,f_y)G_g(f_x-f_o,f_y)$. This term is maximum at $f_x=-2f_o$.

If we were to solve a linear system of N equations like Eq. (34) with N different phase shifts $\phi_n$, then each image having phase shift $\phi_n$ can be expressed by $$G_{is}(f_x, f_y) = \qquad (35)$$

$$\frac{1}{4}|H_1(f_o, 0)|^2\Big[\int\int_\infty H_2(\xi, \eta)H_2^*(\xi - f_x, \eta - f_y) \times G_g(\xi - f_o, \eta)$$

$$G_g^*(\xi - f_o - f_x, \eta - f_y)d\xi d\eta$$

$$\int\int_\infty H_2(\xi, \eta)H_2^*(\xi - f_x, \eta - f_y) \times G_g(\xi + f_o, \eta)$$

$$G_g^*(\xi + f_o - f_x, \eta - f_y)d\xi d\eta\Big] +$$

$$\frac{e^{i2\phi_n}}{4}H_1(f_o, 0)H_1^*(-f_o, 0)\int\int_\infty H_2(\xi, \eta)H_2^*(\xi - f_x, \eta - f_y) \times$$

$$G_g(\xi - f_o, \eta)G_g^*(\xi + f_o - f_x, \eta - f_y)d\xi d\eta +$$

$$\frac{e^{-i2\phi_n}}{4}H_1(-f_o, 0)H_1^*(f_o, 0)\int\int_\infty H_2(\xi, \eta)H_2^*(\xi - f_x, \eta - f_y) \times$$

$$G_g(\xi + f_o, \eta)G_g^*(\xi - f_o - f_x, \eta - f_y)d\xi d\eta$$

for n=1, 2, . . . , N where N≧3. Then in each image equation, we can separate three terms as follows, $$AC(f_x, f_y) = \int\int_\infty H_2(\xi, \eta)H_2^*(\xi - f_x, \eta - f_y)G_g(\xi - f_o, \eta) \qquad (36)$$

$$G_g^*(\xi - f_o - f_x, \eta - f_y)d\xi d\eta + \int\int_\infty H_2(\xi, \eta)$$

$$H_2^*(\xi - f_x, \eta - f_y)G_g(\xi + f_o, \eta)$$

$$G_g^*(\xi + f_o - f_x, \eta - f_y)d\xi d\eta$$

$$= [H_2(f_x, f_y)G_g(f_x - f_o, f_y)] \otimes$$

$$[H_2(f_x, f_y)G_g(f_x - f_o, f_y)] +$$

$$[H_2(f_x, f_y)G_g(f_x + f_o, f_y)] \otimes$$

$$[H_2(f_x, f_y)G_2(f_x + f_o, f_y)]$$

contains a sum of two auto correlations.

$$C^+(f_x, f_y) = \int\int_\infty H_2(\xi, \eta)H_2^*(\xi - f_x, \eta - f_y)G_g(\xi - f_o, \eta) \qquad (37)$$

$$G_g^*(\xi + f_o - f_x, \eta - f_y)d\xi d\eta$$

$$= [H_2(f_x, f_y)G_g(f_x - f_o, f_y)] \otimes$$

$$[H_2(f_x, f_y)G_g(f_x + f_o, f_y)]$$

contains a cross-correlation.

$$C^-(f_x, f_y) = \int\int_\infty H_2(\xi, \eta)H_2^*(\xi - f_x, \eta - f_y)G_g(\xi + f_o, \eta) \qquad (38)$$

$$G_g^*(\xi - f_o - f_x, \eta - f_y)d\xi d\eta$$

$$= [H_2(f_x, f_y)G_g(f_x + f_o, f_y)] \otimes$$

$$[H_2(f_x, f_y)G_g(f_x - f_o, f_y)]$$

also contains another cross-correlation. This linear system of N equations and above three unknowns can be solved using singular value decomposition and pseudoinverse, in a similar fashion as was done for the incoherent case. To solve this we assume prior knowledge of the phase shifts of the sinusoidal illumination in each image or the ability to estimate them a posteriori.

On obtaining the three separable terms in Eqs. (36), (37) and (38), we will need to shift the two cross-correlation terms given by Eqs. (37) and (38) to get the peak of the terms to the origin as was done in the incoherent case using following equations, $$C^+(f_x + 2f_o, f_y) = FT\{e^{-i2\pi(2f_ox)}IFT[C^+(f_x, f_y)]\} \qquad (39)$$

$$= [H_2(f_x + 2f_o, f_y)G_g(f_x + f_o, f_y)] \otimes$$

$$[H_2(f_x, f_y)G_g(f_x + f_o, f_y)]$$

And $$C^-(f_x - 2f_o, f_y) = FT\{e^{i2\pi(2f_ox)}IFT[C^-(f_x, f_y)]\} \qquad (40)$$

$$= [H_2(f_x - 2f_o, f_y)G_g(f_x - f_o, f_y)] \otimes$$

$$[H_2(f_x, f_y)G_g(f_x - f_o, f_y)].$$

The autocorrelations in term 1 already have their peak centered at the origin. Now these separated terms have been shifted to their appropriate positions in frequency space and can be added with appropriate weighting to obtain a reconstructed image, $$I_{rec}(f_x,f_y)=AC(f_x,f_y)+C^+(f_x+2f_o,f_y)+C^-(f_x-2f_o,f_y), \qquad (41)$$

$$I_{rec}(f_x, \qquad (42)$$

$$f_y) = [H_2(f_x, f_y)G_g(f_x - f_o, f_y)] \otimes [H_2(f_x, f_y)G_g(f_x - f_o, f_y)] + [$$

$$H_2(f_x, f_y)G_g(f_x + f_o, f_y)] \otimes [H_2(f_x, f_y)G_g(f_x + f_o, f_y)] + [$$

$$H_2(f_x + 2f_o, f_y)G_g(f_x + f_o, f_y)] \otimes [$$

$$H_2(f_x, f_y)G_g(f_x + f_o, f_y)] + [$$

$$H_2(f_x - 2f_o, f_y)G_g(f_x - f_o, f_y)] \otimes [H_2(f_x, f_y)G_g(f_x - f_o, f_y)].$$

Figure 20:
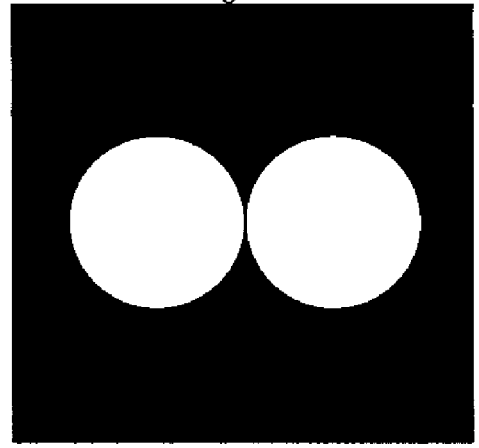
FIG. 20 shows a larger pupil comprising two smaller pupils placed adjacent to each other.

A coherent reflectance image will now be considered. Consider a conventional uniform illumination coherent image taken with a pupil as shown in FIG. 20.

This pupil can be described as, $$H_{eq1}(f_x,f_y)=H_2(f_x-f_o,f_y)+H_2(f_x+f_o,f_y). \qquad (43)$$

The Fourier transform of the field of the image taken from this pupil is given as, $$G_{i_{eq1}}(f_x,f_y)=H_{eq1}(f_x,f_y)G_g(f_x,f_y), \quad (44)$$

$$G_{i_{eq1}}(f_x,f_y)=H_2(f_x-f_o,f_y)G_g(f_x,f_y)+H_2(f_x+f_o,f_y)G_g(f_x,f_y). \quad (45)$$

The Fourier transform of the intensity of this image is given by, $$\mathcal{G}_{i_{eq1}}(f_x,f_y)=G_{i_{eq1}}(f_x,f_y)\otimes G_{i_{eq1}}(f_x,f_y), \quad (46)$$

$$\mathcal{G}_{i_{eq1}}(f_x, f_y) = \qquad (47)$$

$$\int\int_\infty \{[H_2(\xi-f_o-f_x,\eta-f_y)G_g(\xi-f_x,\eta-f_y)+H_2(\xi+f_o-f_x,\eta-f_y)G_g(\xi-f_x,\eta-f_y)]^*[H_2(\xi-f_o,\eta)G_g(\xi,\eta)+H_2(\xi+f_o,\eta)G_g(\xi,\eta)]\}d\xi\,d\eta,$$

$$\mathcal{G}_{i_{eq1}}(f_x, f_y) = \int\int_\infty \{H_2(\xi-f_o,\eta)H_2^*(\xi-f_o-f_x,\eta-f_y) \qquad (48)$$
$$G_g(\xi,\eta)G_g(\xi-f_x,\eta-f_y)^* + H_2(\xi+f_o,\eta)$$
$$H_2^*(\xi+f_o-f_x,\eta-f_y)G_g(\xi,\eta)G_g(\xi-f_x,\eta-f_y)^* +$$
$$H_2(\xi-f_o,\eta)H_2^*(\xi+f_o-f_x,\eta-f_y)G_g(\xi,\eta)$$
$$G_g(\xi-f_x,\eta-f_y)^* + H_2(\xi+f_o,\eta)H_2^*(\xi-f_o-f_x,$$
$$\eta-f_y)G_g(\xi,\eta)G_g(\xi-f_x,\eta-f_y)^*\}d\xi\,d\eta,$$

$$\mathcal{G}_{i_{eq1}}(f_x, f_y) = [H_2(f_x-f_o,f_y)G_g(f_x,f_y)]\otimes[H_2(f_x-f_o,f_y)G_g(f_x,f_y)] + [ \qquad (49)$$
$$H_2(f_x+f_o,f_y)G_g(f_x,f_y)]\otimes[H_2(f_x+f_o,f_y)G_g(f_x,f_y)] + [$$
$$H_2(f_x-f_o,f_y)G_g(f_x,f_y)]\otimes[H_2(f_x+f_o,f_y)G_g(f_x,f_y)] + [$$
$$H_2(f_x+f_o,f_y)G_g(f_x,f_y)]\otimes[H_2(f_x-f_o,f_y)G_g(f_x,f_y)].$$

A conventional coherent image will be compared to the reconstructed image. We compare Eq. (42) with Eq. (49) above. The terms in Eq. (42) can be rewritten as, $$AC(f_x, f_y) = [H_2(f_x,f_y)G_g(f_x-f_o,f_y)]\otimes \qquad (50)$$
$$[H_2(f_x,f_y)G_g(f_x-f_o,f_y)] +$$
$$[H_2(f_x,f_y)G_g(f_x+f_o,f_y)]\otimes$$
$$[H_2(f_x,f_y)G_g(f_x+f_o,f_y)]$$
$$= [H_2(f_x+f_o,f_y)G_g(f_x,f_y)]\otimes$$
$$[H_2(f_x+f_o,f_y)G_g(f_x,f_y)] +$$
$$[H_2(f_x-f_o,f_y)G_g(f_x,f_y)]\otimes$$
$$[H_2(f_x-f_o,f_y)G_g(f_x,f_y)].$$

The second term, $$C^-(f_x+2f_o,f_y) = [H_2(f_x+2f_o,f_y)G_g(f_x+f_o,f_y)]\otimes \qquad (51)$$
$$[H_2(f_x,f_y)G_g(f_x+f_o,f_y)]$$
$$= [H_2(f_x+f_o,f_y)G_g(f_x,f_y)]\otimes$$
$$[H_2(f_x-f_o,f_y)G_g(f_x,f_y)].$$

Similarly the third term, $$C^-(f_k-2f_o,f_y) = [H_2(f_x-2f_o,f_y)G_g(f_x-f_o,f_y)]\otimes \qquad (52)$$
$$[H_2(f_x,f_y)G_g(f_x-f_o,f_y)]$$
$$= [H_2(f_x-f_o,f_y)G_g(f_x,f_y)]\otimes$$
$$[H_2(f_x+f_o,f_y)G_g(f_x,f_y)].$$

Therefore, from Eq. (41), adding Eqs. (50), (51) and (52) we get, $$I_{rec}(f_x, f_y) = [H_2(f_x+f_o,f_y)G_g(f_x,f_y)]\otimes \qquad (53)$$
$$[H_2(f_x+f_o,f_y)G_g(f_x,f_y)] + [H_2(f_x-f_o,f_y)G_g(f_x,f_y)]\otimes$$
$$[H_2(f_x-f_o,f_y)G_g(f_x,f_y)] + [H_2(f_x+f_o,f_y)G_g(f_x,f_y)]\otimes$$
$$[H_2(f_x-f_o,f_y)G_g(f_x,f_y)] + [H_2(f_x-f_o,f_y)G_g(f_x,f_y)]\otimes[H_2(f_x+f_o,f_y)G_g(f_x,f_y)].$$

This reconstructed image is identical to the conventional uniformly illuminated coherent image taken with the double pupil shown in Eq. (49). Therefore we conclude that this reconstructed image contains superresolution along the horizontal $f_x$ axis in spatial frequency space. If multiple coherent speckle realizations of such an image are summed, we obtain an incoherent image with superresolution along the horizontal $f_x$ axis in spatial frequency space.

Now if the same is repeated with the sinusoidal patterned illumination rotated by, say, 60° and 120°, the effective incoherent reconstructions will contain superresolution along the 60° and 120° in spatial frequency space respectively. These three incoherent reconstructions may now be summed together to obtain superresolution in all directions in Fourier space. The inverse Fourier transform of this sum would give an image with superresolution. It should be noted that for low values of spatial frequency of the sinusoidal illumination giving lower superresolution even two orientations, such as, 0° and 90°, suffice to get superresolution in all directions in Fourier space.

Axial sectioning with sinusoidal illumination will now be disclosed. Axial sectioning has been obtained by taking widefield images of the object illuminated by a sinusoidally patterned illumination. Here we assume that the object is stationary. Three or more images are taken with the phase of the sinusoidal patterned illumination shifted by distinct amounts. So the object is the same in these three images and the phase shifts in the sinusoidal illumination impart diversity to the images. Now these three images are processed to obtain a sectioned image.

Image formation is accomplished in the following manner. Consider a sinusoidally patterned fringe illuminating the object. We specifically consider a vertical sinusoidal pattern of spatial frequency $f_o$ and phase shift $\phi_n$. The field of this illumination is $$U_s(x,y)=\cos(2\pi f_o x+\phi_n). \qquad (54)$$

Its intensity is given as $$I_s(x, y) = \frac{1}{2}[1+\cos(4\pi f_o x + 2\phi_n)]. \qquad (55)$$

Let us introduce a constant m to allow for incoherent grating illumination, $$I_s(x, y) = \frac{1}{2}[1 + m\cos(4\pi f_o x + 2\phi_n)]. \quad (56)$$

Usually we can set m=1 assuming high contrast fringes. We assume that $U_g$ is the field of the object transmittance or reflectance; $h_1$ and $h_2$ are the illumination and imaging coherent impulse response functions. For a fluorescent object the object intensity is given by $I_g$.

The image of such a sinusoidally illuminated object is known in the art to be given as, $$I_n(x,y) = \iint [1+m\cos(4\pi f_o x_0 + 2\phi_n)]|\iint h_1(x_0+x_1,y_0+y_1)U_g(x_1,y_1) \times h_2(x_1+x,y_1+y)dx_1 dy_1|^2 dx_0 dy_0. \quad (57)$$

We further simplify this equation using the particular case of a fluorescent object with intensity $I_g$ and obtain the following equation, $$I_n(x,y) = \iiiint [1+m\cos(4\pi f_o x_0 + 2\phi_n)]I_g(x_1,y_1)|h_1(x_0+x_1,y_0+y_1) \times h_2(x_1+x,y_1+y)|^2 dx_1 dy_1 dx_0 dy_0, \quad (58)$$

$$I_n(x,y) = \{\{[1+m\cos(4\pi f_o x + 2\phi_n)]*|h_1(x,y)|^2\} \times I_g(x,y)\}*|h_2(x,y)|^2. \quad (59)$$

This simplification is justified as known in the prior art. And Eq. (58) can also be written as $$I_n(x,y) = I_o(x,y) + I_c(x,y)\cos(2\phi_n) + I_s(x,y)\sin(2\phi_n), \quad (60)$$

where $$I_o(x,y) = \iiiint I_g(x_1,y_1)|h_1(x_0+x_1,y_0+y_1)h_2(x_1+x,y_1+y)|^2 dx_1 dy_1 dx_0 dy_0, \quad (61)$$

$$I_o(x,y) = c_1 I_g(x,y) * |h_2(x,y)|^2, \quad (62)$$

which is same as a conventional image and where $$c_1 = \iint |h_1(x_0+x_1,y_0+y_1)|^2 dx_0 dy_0. \quad (63)$$

Now, $$I_c(x,y) = m\iiiint I_g(x_1,y_1)|h_1(x_0+x_1,y_0+y_1) \times h_2(x_1+x,y_1+y)|^2 dx_1 dy_1 \cos(4\pi f_o x_0) dx_0 dy_0, \quad (64)$$

$$I_c(x,y) = m\{[\cos(4\pi f_o x) * |h_1(x,y)|^2] \times I_g(x,y)\} * |h_2(x,y)|^2, \quad (65)$$

and $$I_s(x,y) = -m\iiiint I_g(x_1,y_1)|h_1(x_0+x_1,y_0+y_1) \times h_2(x_1+x,y_1+y)|^2 dx_1 dy_1 \sin(4\pi f_o x_0) dx_0 dy_0, \quad (66)$$

$$I_s(x,y) = -m\{[\sin(4\pi f_o x) * |h_1(x,y)|^2] \times I_g(x,y)\} * |h_2(x,y)|^2. \quad (67)$$

The sectioned image is obtained in the prior art by using three images—$I_1$ at 0°, $I_2$ at 120° and $I_3$ at 240° phase shifts in the sinusoidal illumination using, $$I_p(x, y) = \sqrt{[I_1(x, y) - I_2(x, y)]^2 + [I_1(x, y) - I_3(x, y)]^2 + [I_2(x, y) - I_3(x, y)]^2}. \quad (68)$$

This equation can also be written as, $$I_p(x,y) = \sqrt{I_c^2(x,y) + I_s^2(x,y)}, \quad (69)$$

$$I_p(x,y) = |I_c(x,y) + iI_s(x,y)|. \quad (70)$$

We can rewrite Eq. (70) as $$I_p(x,y) = |IFT\{FT[I_c(x,y)] + iFT[I_s(x,y)]\}|. \quad (71)$$

In the Fourier domain the imaging and illumination path optical transfer functions are given by $H_1$ and $H_2$ and $G_g$ is the Fourier transform of the object intensity. If we consider the value of $I_c$ in the Fourier domain, using Eq. (65) we get $$FT[I_c] = \frac{m}{2}[\mathcal{H}_2(f_x, f_y)\mathcal{H}_1(2f_o, 0)\mathcal{G}_g(f_x - 2f_0, f_y) + \mathcal{H}_2(f_x, f_y)\mathcal{H}_1(-2f_o, 0)\mathcal{G}_g(f_x + 2f_0, f_y)]. \quad (72)$$

Similarly the Fourier transform of $I_s$ from Eq. (67) is given by $$FT[I_s] = -i\frac{m}{2}[\mathcal{H}_2(f_x, f_y)\mathcal{H}_1(2f_o, 0)\mathcal{G}_g(f_x - 2f_0, f_y) - \mathcal{H}_2(f_x, f_y)\mathcal{H}_1(-2f_o, 0)\mathcal{G}_g(f_x + 2f_0, f_y)]. \quad (73)$$

Using Eq. (71) we can derive that the sectioned image is given by, $$I_p(x,y) = m|IFT[H_1(2f_o,0)H_2(f_x,f_y)G_g(f_x - 2f_o,f_y)]|, \quad (74)$$

where m and $H_1(2f_o,0)$ are clumped into a constant, $$c_2 = mH_1(2f_o,0), \quad (75)$$

giving us the sectioned image, $$I_p(x,y) = c_2|IFT[H_2(f_x,f_y)G_g(f_x - 2f_o,f_y)]|. \quad (76)$$

Now consider the structured illumination image given in Eq. (59) in the Fourier domain, $$\mathcal{G}_n(f_x, f_y) = \mathcal{H}_1(0, 0)\mathcal{H}_2(f_x, f_y)\mathcal{G}_g(f_x, f_y) + \frac{m}{2}\mathcal{H}_1(2f_o, 0)e^{i2\phi_n}\mathcal{H}_2(f_x, f_y)\mathcal{G}_g(f_x - 2f_o, f_y) + \frac{m}{2}\mathcal{H}_1(-2f_o, 0)e^{-i2\phi_n}\mathcal{H}_2(f_x, f_y)\mathcal{G}_g(f_x + 2f_o, f_y). \quad (77)$$

Figure 21:
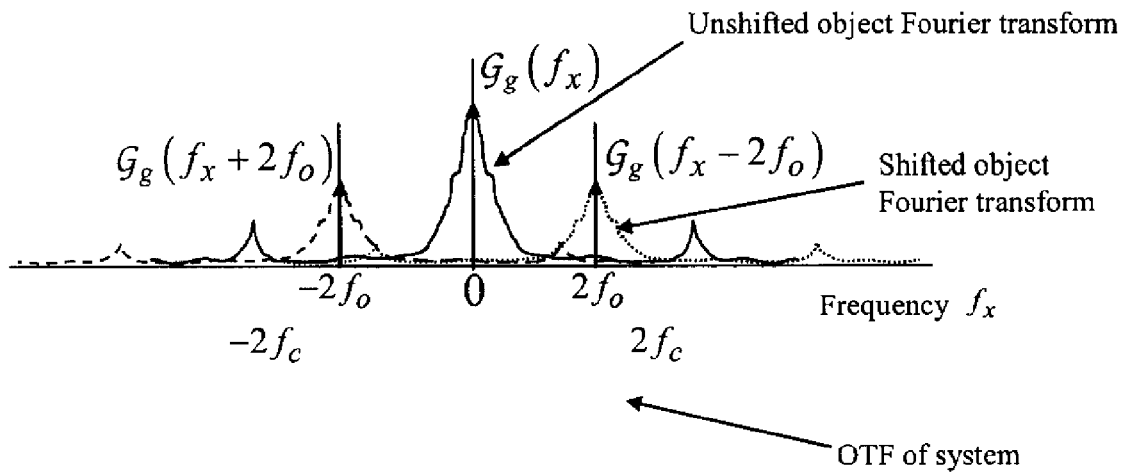
FIG. 21 is a plot of a visualization of sinusoidally patterned fringe illuminated image in Fourier domain.

This equation can be visualized as depicted in FIG. 21. This image shows that Eq. (77) consists of three superimposed copies of the object Fourier transform: $H_2(f_x,f_y)G_g(f_x,f_y)$, which is the unshifted conventional image, $H_2(f_x,f_y)G_g(f_x-2f_o,f_y)$ and $H_2(f_x,f_y)G_g(f_x+2f_o,f_y)$, which are copies of the object Fourier transform displaced to be centered at the spatial frequency of the sinusoidal fringe illumination.

Figure 22:
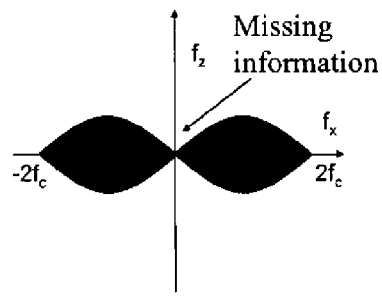
FIG. 22 shows the 3-D OTF of a microscope.

If we consider Eq. (76) we note that the sectioned image is given by the magnitude of the inverse Fourier transform of one of the shifted object spectrum terms. The 3-D optical transfer function of a microscope, shown in FIG. 22, shows a missing gap ("cone") of information along the $f_z$ axis.

Figure 23:
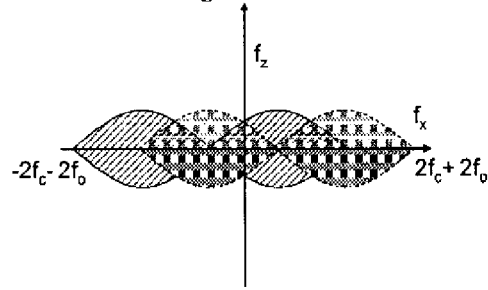
FIG. 23 shows the 3-D OTF of a sectioned image in which shifted OTFs fill in the missing gap in the conventional OTF.
Figure 24:
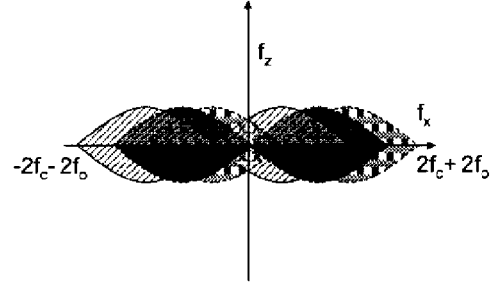
FIG. 24 shows shifted and unshifted spectra all added together.

This missing gap along the $f_z$ axis can be filled in if we consider an image formed by using shifted OTFs as shown in FIG. 23. Here the shifted OTFs fill in the missing cone of information present in a conventional 3-D OTF. The sum is shown in FIG. 24.

Equation (76) shows that the sectioned image comprises of the absolute of the inverse Fourier transform of the shifted version of the object spectrum. This effectively shifts the OTF of the imaging system in Fourier domain. Therefore, Eq. (76)

actually is an image formed by shifted overlapping versions of the OTF. This shift is proportional to the spatial frequency of the sinusoidal illumination with respect to the cutoff frequency of the system.

Now we discuss phase shift estimation. Three or more such images are taken with the phase of the sinusoidal fringe patterned illumination shifted by distinct amounts. If one can control the phase shifts introduced precisely then it is common to use equally spaced phase shifts $$\frac{2\pi}{N}(n-1)$$

where N is the total number of sinusoidally patterned images being taken and n is the index of each image, given by n=1, 2, . . . N.

We particularly consider the case of a rigid, randomly translating object as our specimen. In this case the object could translate randomly between successive N sinusoidally illuminated image frames. Therefore it is not possible in this case to introduce precisely known phase shifts of equal step size. The object is registered and aligned in successive sinusoidally patterned images. The effective phase shifts in the sinusoidal illumination are random and unknown and must be estimated a posteriori. We estimate the phase shift in each sinusoidally patterned image by using the equation below, $$\phi_n = \frac{1}{2}\tan^{-1}\left\{\frac{imag[\mathcal{G}_n(2f_o, 0)]}{real[\mathcal{G}_n(2f_o, 0)]}\right\}, \quad (78)$$

where arctangent is the a tan 2 function in Matlab, which gives a phase between $-\pi$ to $\pi$. Here we look at the phase of the Fourier transform of the sinusoidally patterned image at the peak produced by the sinusoidal illumination. For our assumption of a vertical sinusoidal illumination field of spatial frequency $f_o$ we look at the phase of the image at $(2f_o, 0)$. This can be generalized to any rotated sinusoidal illumination for any generalized frequency $(f_{xo}, f_{yo})$.

Object spectrum segregation will now be considered. After estimating these unknown phase shifts it is possible to separate the three overlapping replicas of the object Fourier transform from these N images by considering the set of N sinusoidally patterned images as a linear system of equations, $$AX=B, \quad (79)$$

where, $$A = \begin{bmatrix} \mathcal{H}_1(0,0) & \frac{m}{2}\mathcal{H}_1(2f_o,0)e^{i2\phi_1} & \frac{m}{2}\mathcal{H}_1(-2f_o,0)e^{-i2\phi_1} \\ \mathcal{H}_1(0,0) & \frac{m}{2}\mathcal{H}_1(2f_o,0)e^{i2\phi_2} & \frac{m}{2}\mathcal{H}_1(-2f_o,0)e^{-i2\phi_2} \\ \vdots & \vdots & \vdots \\ \mathcal{H}_1(0,0) & \frac{m}{2}\mathcal{H}_1(2f_o,0)e^{i2\phi_N} & \frac{m}{2}\mathcal{H}_1(-2f_o,0)e^{-i2\phi_N} \end{bmatrix}_{N\times 3}, \quad (80)$$

$$X = \begin{bmatrix} \mathcal{H}_2(f_x, f_y)\mathcal{G}_g(f_x, f_y) \\ \mathcal{H}_2(f_x, f_y)\mathcal{G}_g(f_x - 2f_o, f_y) \\ \mathcal{H}_2(f_x, f_y)\mathcal{G}_g(f_x + 2f_o, f_y) \end{bmatrix}_{3\times 1}, \quad (81)$$

$$B = \begin{bmatrix} \mathcal{G}_1(f_x, f_y) \\ \mathcal{G}_2(f_x, f_y) \\ \vdots \\ \mathcal{G}_N(f_x, f_y) \end{bmatrix}_{N\times 1}. \quad (82)$$

If all the elements in matrix A are known, we solve for matrix X which is the matrix of desired unknown overlapping replicas of the object Fourier transforms by finding the singular value decomposition and pseudoinverse of matrix A and premultiply that to B.

Now in the case of optical sectioning, if we take the second or third elements in matrix X and use Eq. (76) we can obtain an optically sectioned image of the object. It should be noted that these terms can also be used to obtain lateral superresolution.

Figure 25:
FIG. 25 shows a conventional widefield fluorescence image of object.

Experimental results will now be disclosed. We took several images of a fluorescent biological specimen on a widefield Zeiss Axio Imager microscope. FIG. 25 shows a conventional widefield fluorescence image.

Figure 26:
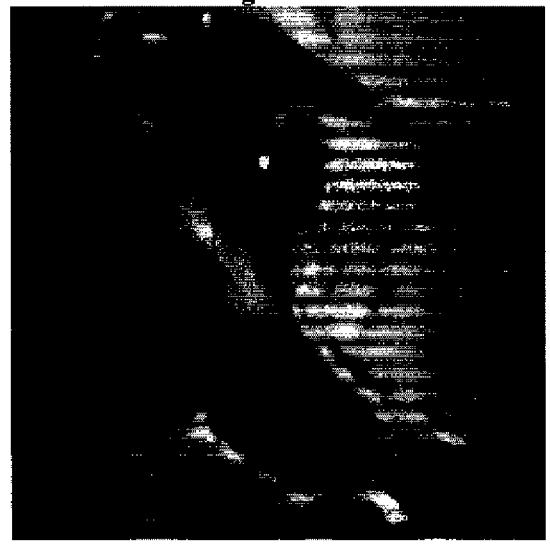
FIG. 26 shows a grid patterned illumination image of an object.

We also took several images of the same object with an ApoTome attachment on this microscope. This attachment introduces a grid in the illumination path producing a grid patterned illumination. This attachment was used to produce several grid illuminated images of this object such as shown in FIG. 26 with the phase of the grid in the illumination shifted by random unknown amounts.

Figure 27:
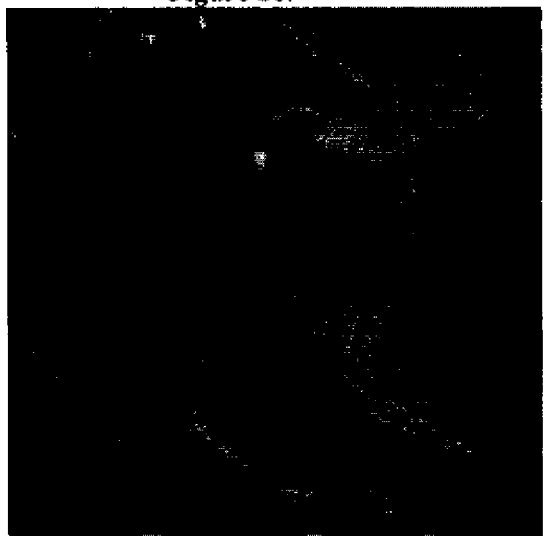
FIG. 27 shows a sectioned image obtained by our technique.

We used four randomly chosen grid patterned images, estimated the unknown phase shifts a posteriori using Eq. (18). Using these phase shifts and Eq. (79)-Eq. (82) we were able to segregate the three overlapping object spectra. Then we used Eq. (76) to obtain a sectioned image of the specimen shown in FIG. 27.

Our sectioned image was corroborated with the sectioned image generated by the Zeiss ApoTome shown in FIG. 28. The Zeiss ApoTome image is produced with three grid patterned images having fixed, known phase shifts of 0°, 120° and 240°.

Our image is comparable to the Zeiss ApoTome image. It should be noted that there are some residual fringe artifacts in both sectioned images. This could be due to the fact that the grid is actually a rectangular grating and hence has some higher harmonics leaking into the image. We have not accounted for these in our calculations, but they can be corrected by using known techniques.

But we also note that our sectioned image has some more residual fringe artifacts compared to the ApoTome image. The grid internal to the ApoTome moves continuously and we have no control over its motion to pause it during imaging. We also have no access to the integration time information of grid patterned images taken internally by the ApoTome. Hence we believe that our residual fringe patterned artifacts are due to the longer integration time in our grid patterned images compared to the images probably taken by the ApoTome.

Our method of obtaining axial sectioning requires no prior knowledge about the phase shifts in the sinusoidal illumination and can handle random phase shifts. Hence this can be used for in vivo objects which show random, unknown, rigid body translational motion. The object in such images can be registered and aligned. Now the effective phase shift in the sinusoidal illumination can be estimated and the overlapping object spectra can be segregated. The shifted spectra can be used to obtain a sectioned image.

FIG. 29 shows a setup on which the preferred or other embodiments can be implemented. While the figure shows such a setup as used for retinal imaging, those skilled in the art who have reviewed the present disclosure will readily appreciate that an essentially similar setup can be used for any sort of in vivo, in vitro, or non-biological imaging. In the setup 1, light L from a light source 3 passes through a grating 5 (or any other fringe interference pattern generation element) that can be moved by a translation stage or other motor 7. The element 7 could also be any suitable phase shifting element, such as a phase plate or another suitable component for an interferometer. For that matter, the object itself could be moved instead of, or in addition to, the use of a phase shifting element. In fact, in the case of a moving object, the movement supplies at least part of the phase shift. The light passes through a beamsplitter 9 and impinges on the retina R of the eye E or other object to be imaged. Light reflected by the retina is reflected by the beamsplitter onto a detector 11, which produces image data and sends them to a processor 13. The processor 13 carries out the operations described above and outputs the resulting image to an output 15, which can be one or more of a display, a printer, and a storage medium. The illumination may be produced by a grating in front of a light source in some incoherent manner or coherently by producing interference fringes with a laser. The present invention is applicable to both cases and to any combination of laser/light source and grating or interference. The estimated phase shifts can be fed back to calibrate the phase shifts applied by the phase shifting element 7. In the case of coherent illumination of a non-fluorescent object, one could reduce speckle, an artifact of coherent imaging, by changing the angle of illumination of the object while maintaining the same periodicity in the illumination pattern.

While preferred embodiments of the present invention have been set forth above, those skilled in the art who have reviewed the present disclosure will readily appreciate that other embodiments can be realized within the scope of the invention. Some variations have been set forth above. As examples of others, numerical values are illustrative rather than limiting, as are recitations of specific hardware and software. Therefore, the invention should be construed as limited only by the appended claims.

We claim:

1. A method for imaging an object, the method comprising:
    (a) applying a structured periodic illumination to the object a plurality of times with a plurality of phase shifts of the structured illumination caused by relative movement between the structured illumination and the object;
    (b) taking a plurality of images of the object corresponding to the plurality of phase shifts;
    (c) estimating the plurality of phase shifts by determining a phase of a peak of a Fourier transform of each of the images taken in step (b) by a processor; and
    (d) reconstructing a 2-D image or 3-D image of the object using the plurality of images taken in step (b) and the plurality of phase shifts estimated in step (c).

2. The method of claim 1, wherein the object is stationary during step (b).

3. The method of claim 2, wherein the object is fluorescent.

4. The method of claim 3, wherein step (a) is performed with coherent illumination.

5. The method of claim 3, wherein step (a) is performed with non-coherent illumination.

6. The method of claim 2, wherein the object is non-fluorescent.

7. The method of claim 6, wherein step (a) is performed with coherent illumination.

8. The method of claim 6, wherein step (a) is performed with non-coherent illumination.

9. The method of claim 1, wherein the object is non-stationary during step (b).

10. The method of claim 9, wherein the object is fluorescent.

11. The method of claim 10, wherein step (a) is performed with coherent illumination.

12. The method of claim 10, wherein step (a) is performed with non-coherent illumination.

13. The method of claim 9, wherein the object is non-fluorescent.

14. The method of claim 13, wherein step (a) is performed with coherent illumination.

15. The method of claim 13, wherein step (a) is performed with non-coherent illumination.

16. The method of claim 9, wherein the phase shifts estimated in step (c) are caused at least partially by movement of the object.

17. The method of claim 1, wherein the object is fluorescent.

18. The method of claim 1, wherein step (a) is performed with coherent illumination.

19. The method of claim 18, wherein step (a) comprising changing an angle of illumination of the object to reduce speckle.

20. The method of claim 1, wherein step (a) is performed with non-coherent illumination.

21. The method of claim 1, wherein the object is non-fluorescent.

22. The method of claim 1, wherein step (a) is performed with coherent illumination.

23. The method of claim 1, wherein step (a) is performed with non-coherent illumination.

24. The method of claim 1, wherein step (d) comprises forming a lateral superresolution image of the object.

25. The method of claim 1, wherein step (d) comprises forming an axially sectioned image of the object.

26. The method of claim 25, wherein step (d) further comprises forming a lateral superresolution image of the object.

27. The method of claim 1, wherein step (a) comprises applying the structured periodic illumination at a plurality of angular orientations.

28. The method of claim 1, wherein the phase shifts estimated in step (c) are caused at least partially by moving an optical element.

29. The method of claim 1, wherein the phase shifts estimated in step (c) are caused at least partially by moving the object.

30. The method of claim 1, wherein the phase shifts estimated in step (c) are used in phase shift calibrations.

31. A system for imaging an object, the system comprising:
    optics for applying a structured periodic illumination to the object a plurality of times with a plurality of phase shifts of the structured illumination caused by relative movement between the structured illumination and the object;
    an imaging device for taking a plurality of images of the object corresponding to the plurality of phase shifts; and
    a processor, in communication with the imaging device, for estimating the plurality of phase shifts by determining a phase of a peak of a Fourier transform of each of the images and reconstructing a 2-D image or 3-D image of the object using the plurality of images and the plurality of phase shifts.

32. The system of claim 31, wherein the optics comprise a source of coherent illumination.

33. The system of claim 32, wherein the optics comprise an optical element for forming interference fringes on the object.

34. The system of claim 33, wherein the optics comprise a grating.

35. The system of claim 31, wherein the optics comprise a source of non-coherent illumination.

36. The system of claim 31, wherein the processor forms a lateral superresolution image of the object.

37. The system of claim 31, wherein the processor forms an axially sectioned image of the object.

38. The system of claim 37, wherein the processor also forms a lateral superresolution image of the object.

39. The system of claim 31, wherein the optics apply the structured periodic illumination at a plurality of angular orientations.

40. The system of claim 31, wherein the optics comprise an optical element that is controllable to apply the plurality of phase shifts.

41. The system of claim 40, wherein the optics further comprise a device for moving the optical element to apply the plurality of phase shifts.

42. The system of claim 41, wherein the optical element comprises a grating.

43. The system of claim 31, further comprising a device for moving the object to apply the plurality of phase shifts.

44. The system of claim 31, wherein the estimated phase shifts are used in phase shift calibrations.

45. The method of claim 1, wherein, in step (c), the Fourier transform is a spatial-frequency Fourier transform.

46. The system of claim 31, wherein the processor is configured such that the Fourier transform is a spatial-frequency Fourier transform.

* * * * *